US006277578B1

(12) United States Patent
Shultz et al.

(10) Patent No.: US 6,277,578 B1
(45) Date of Patent: *Aug. 21, 2001

(54) DEPLOYMERIZATION METHOD FOR NUCLEIC ACID DETECTION OF AN AMPLIFIED NUCLEIC ACID TARGET

(75) Inventors: John William Shultz, Verona; Martin K. Lewis, Madison; Donna Leippe, Middleton; Michelle Mandrekar, Oregon; Christine Ann Andrews, Cottage Grove; James Robert Hartnett, Madison, all of WI (US); Roy Welch, Palo Alto, CA (US)

(73) Assignee: Promega Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/430,615

(22) Filed: Oct. 29, 1999

Related U.S. Application Data

(63) Continuation-in-part of application No. 09/358,972, filed on Jul. 21, 1999, which is a continuation-in-part of application No. 09/252,436, filed on Feb. 18, 1999, now Pat. No. 6,159,693, which is a continuation-in-part of application No. 09/042,287, filed on Mar. 13, 1998.

(51) Int. Cl.[7] .............................. C12Q 1/68; C12P 19/34; C07H 21/02

(52) U.S. Cl. ............................ 435/6; 435/91.1; 435/91.2

(58) Field of Search ................................. 435/5, 6, 91.2

(56) References Cited

U.S. PATENT DOCUMENTS

| 4,446,231 | 5/1984 | Self ........................................... 435/7 |
| 4,460,684 | 7/1984 | Bauer ....................................... 435/14 |
| 4,595,655 | 6/1986 | Self ........................................... 435/7 |
| 4,683,202 | 7/1987 | Mullis et al. ........................... 435/91 |
| 4,735,897 | 4/1988 | Vary et al. ............................... 435/17 |
| 4,743,561 | 5/1988 | Shaffar ................................... 436/501 |
| 4,755,458 | 7/1988 | Rabbani et al. ......................... 435/5 |
| 4,800,159 | 1/1989 | Mullis et al. ....................... 435/172.3 |
| 4,863,195 | 9/1989 | Mullis et al. ............................. 435/6 |
| 5,389,512 | 2/1995 | Sninsky et al. .......................... 435/5 |
| 5,399,491 | 3/1995 | Kacian et al. ............................ 435/6 |
| 5,445,933 | 8/1995 | Eadie et al. .............................. 435/6 |
| 5,494,810 * | 2/1996 | Barany et al. ..................... 435/91.52 |
| 5,498,523 | 3/1996 | Tabor et al. .............................. 435/6 |
| 5,512,439 | 4/1996 | Hornes et al. ............................ 435/6 |
| 5,516,663 | 5/1996 | Backman et al. .................... 435/91.2 |
| 5,530,192 * | 6/1996 | Murase et al. ......................... 800/205 |
| 5,561,044 | 10/1996 | Walker et al. ............................ 435/6 |
| 5,573,906 | 11/1996 | Bannwarth et al. ...................... 435/6 |
| 5,579,820 | 12/1996 | Hornes et al. ......................... 435/91.1 |
| 5,622,824 * | 4/1997 | Koster et al. ............................. 435/6 |
| 5,648,232 | 7/1997 | Squirrell .................................. 435/34 |
| 5,667,964 | 9/1997 | Ho ............................................ 435/5 |
| 5,683,877 * | 11/1997 | Lu-Chang et al. ........................ 435/6 |
| 5,691,146 | 11/1997 | Mayrand .................................. 435/6 |
| 5,723,591 | 3/1998 | Livak et al. ............................ 536/22.1 |
| 5,736,365 | 4/1998 | Walker et al. ......................... 435/91.2 |
| 5,741,635 * | 4/1998 | Boss et al. ................................. 435/4 |
| 5,763,181 * | 6/1998 | Han et al. ................................. 435/6 |
| 5,766,849 | 6/1998 | McDonough et al. ................... 435/6 |
| 5,786,183 | 7/1998 | Ryder et al. .......................... 435/91.2 |
| 5,814,491 | 9/1998 | Vijg et al. ............................. 435/91.2 |
| 5,824,517 | 10/1998 | Cleuziat et al. ...................... 435/91.2 |
| 5,834,202 | 10/1998 | Auerbach ................................. 435/6 |
| 5,840,873 | 11/1998 | Nelson et al. ....................... 536/24.3 |
| 5,843,660 | 12/1998 | Schumm et al. ......................... 435/6 |
| 5,849,487 * | 12/1998 | Hase et al. ............................... 435/6 |
| 5,849,547 | 12/1998 | Cleuziat et al. .................... 435/91.21 |
| 5,853,981 | 12/1998 | Kondo et al. ............................ 435/5 |
| 5,854,033 | 12/1998 | Lizardi ................................. 435/91.2 |
| 5,861,242 | 1/1999 | Chee et al. ............................... 435/5 |
| 5,863,736 | 1/1999 | Haaland ................................... 435/6 |
| 5,866,337 | 2/1999 | Schon ...................................... 435/6 |
| 5,869,252 | 2/1999 | Bouma et al. ............................ 435/6 |
| 5,876,924 | 3/1999 | Zhang et al. ............................. 435/5 |
| 5,876,930 | 2/1999 | Livak et al. .............................. 435/6 |
| 5,876,978 | 3/1999 | Willey et al. ........................ 435/91.2 |
| 5,880,473 | 3/1999 | Ginestet ............................. 250/458.1 |
| 5,882,856 | 3/1999 | Shuber .................................... 435/6 |
| 5,885,775 | 3/1999 | Haff et al. ................................ 435/6 |
| 5,888,819 | 3/1999 | Goelet et al. ............................. 435/5 |

FOREIGN PATENT DOCUMENTS

| 2055200 | 12/1981 | (GB) .............................. G01N/21/76 |
| WO 94/25619 | 11/1994 | (WO) .............................. C12Q/1/00 |
| WO96/41014 * | 12/1996 | (WO) .............................. C12Q/1/68 |
| WO 98/13523 | 4/1998 | (WO) .............................. C12Q/1/68 |
| WO 98/28440 | 7/1998 | (WO) .............................. C12Q/1/68 |

OTHER PUBLICATIONS

R. P. Agarwal et al., "Nucleoside Diphosphokinase from Human Erythrocytes", *Methods in Enzymology*, vol. 51, pp. 376–386 (1978).*

Cantor & Schimmel, "Biophysical Chemistry", vol. II, pp. 381–385 (1980).*

A.E. Sippel, "Purification and Characterization of Adenosine Triphosphate: Ribonucleic Acid Adenyltransferase from *Escherchia coli*" *Eur. J. Biochem.* 37:31–40 (1973).

K.Chowdhury, N. Kaushik, V.N. Pandey and M.J. Modak, "Elucidiation of the Role of Arg 110 of Murine Leukemia Virus Reverse Transcriptase in the Catalytic Mechanism: Biochemical Characterization of Its Mutant Enzymes," *Biochemistry*, 35:16610–16620 (1996).

S. Karamohamed, M. Ronaghi and P. Nyren, "Bioluminometric Method for Real–Time Detection of Reverse Transcriptase Activity", *Biotechniques*, 24:302–306 (Feb., 1998).

(List continued on next page.)

*Primary Examiner*—Kenneth R. Horlick
*Assistant Examiner*—Teresa Strzelecka
(74) *Attorney, Agent, or Firm*—Welsh & Katz, Ltd.

(57) ABSTRACT

The detection of enhanced, targeted predetermined nucleic acid sequences in nucleic acid target hybrids, and the various applications of target nucleic acid enhancement are disclosed.

62 Claims, 1 Drawing Sheet

OTHER PUBLICATIONS

B. Hove–Jensen, K.W. Harlow, C.J. King, R.L. Switzer, "Phosphoribosylpyrophosphate Synthetase of *Escherichia coli*", *J. Biol. Chem.*, 261(15):6765–6771 (1986).

P. Nyren, S. Karamohamed and M. Ronaghi, "Detection of Single–Base Changes Using a Bioluminometric Primer Extension Assay", *Anal. Biochem.*, 244:367–373 (Jan. 15, 1997).

M. Ronaghi, S. Karamohamed, B. Pettersson, M. Uhlen and P. Nyren, "Real–Time DNA Sequencing Using Detection of Pyrophosphate Release," *Anal. Biochem.*, 242:84–89 (1996).

T.A. Rozovskaya, V.O. Rechinsky, R.S. Bibilashvili, M.Y. Karpeisky, N.B. Tarusova, R.M. Khomutov, H.B.F. Dixon, "The Mechanism of Pyrophosphorolysis of RNA by RNA Polymerase", *Biochem. J.*, 224:645–650 (1989).

M.P. Deutscher and A. Kornberg, "Enzymatic Synthesis of Deoxyribonucleic Acid", *J. Biol. Chem.*, 244(11):3019–28 (1969).

J.D. Moyer and J.F. Henderson, "Nucleoside Triphosphate Specificity of Firefly Luciferase", *Anal. Biochem.*, 131:187–189 (1983).

C. Blondin, L. Serina, L. Weismuller, A. Gilles and O. Barzu, "Improved Spectrophotometric Assay of Nucleoside Monophosphate Kinase Activity Using the Pyruvate Kinase/Lactate Dehydrogenase Coupling System", *Anal. Biochem.*, 220:219–21 (1994).

S. Tabor and C.C. Richardson, "DNA Sequence Analysis With a Modified Bacteriphage T7 DNA Polymerase", *J. Biol. Chem.*, 265(14):8322–8328 (1990).

R.S. Chittock, J.–M. Hawronsky, J. Holah and C.W. Wharton, "Kinetic Aspects of ATP Amplification Reactions", *Anal. Biochem.*, 255:120–126 (Jan. 1, 1998).

Kung, et al., "Picogram Quantitation ofTotal DNA Using DNA–Binding Proteins in a Silicon Sensor–Based System", *Anal. Biochem.*, 187:220–227 (1990).

Srivastavan & Modak, *J. Biol. Chem.*, 255(5):2000–2004 (1980).

Sano & Feix, *Eur. J. Biochem*, 71:577–583 (1976).

Sabina, et al., *Science*, 223:1193–1195 (1984).

Parks & Agarwal in *The Enzymes*, vol. 9:307–333, P. Boyer Ed. (1973).

Shimofuruya & Suzuki, *Biochem. Intl.*, 26(5):853–861 (1992).

Nyren, et al., "Detection of Single–Base Changes Using a Bioluminometric Primer Extension Assay", *Anal. Biochem.*, 244:367–373 (1997).

P. Bernard et al., *Am. J. Pathol.*, 153:1055–1061 (1998).

G. Garinis et al., *J. Clin. Lab. Anal.*, 13:122–125 (1999).

Holguin, et al., *Eur. J. Clin. Microbiol. Infect. Dis.*, 18:256–259 (1999).

Boriskin, et al., *Arch. Dis. Child.*, 80:132–136 (1999).

de Vega, et al., "Primer Terminus Stabilizing at the 3'–5' exonuclease active site of _29 DNA polymerase. Involvement of two amino acid residues highly conserved in proofreading DNA polymerases", *EMBO J.*, 15(5):1182–1192 (1996).

S. Patel et al., *Biochemistry*, 30:511–525 (1991).

I. Wong et al., *Biochemistry*, 30:526–537 (1991).

S. Zinnen et al., *J. Biological Chemistry*, 269(39):24195–24202 (1994).

J. Lindquist, Dept. of Bacteriology, University of Wisconsin–Madison, http://www.bact.wisc.edu/bact102/102dil3.html.

J. Lindquist, Dept. of Bacteriology, University of Wisconsin–Madison, http://www.bact.wisc.edu/bact102/102dil3a.html.

Most Probable Number (MPN), WQA Glossary of Terms, 3rd Ed., Water Quality Association.

P. Nyren, B. Pettersson, and M. Uhlen. "Solid Phase DNA Minisequencing by an Enzymatic Luminometric Inorganic Pyrophosphate Detection Assay," *Anal. Biochem.*, 208:171–175 (1993).

M. Ronaghi, S. Karamohamed, B. Pettersson, M. Uhlen, and P. Nyren, "Real–Time DNA Sequencing Using Detection of Pyrophosphate Release," *Anal. Biochem.*, 242:84–89 (1996).

J. Shultz, D. Leippe, K. Lewis, R. Lyke, M. Nelson, and C. Reynolds., "Detection of Low Levels of Nucleic Acids by Enzymatic Conversion to Substrates for Luciferase", Poster presented Jul. 25–29, 1998 at a Protein Society meeting in San Diego, California.

Heid, et al., "Real Time Quantitative PCR", *Genome Research*, 6:986–994 (1996).

Nagano, et al., "Detection of Verotoxin–Producing *Escherichia coli* O157:H7 by Multiplex Polymerase Chain Reaction", *Microbiol. Immunol.*, 42(5), 372–376 (1998).

Sherlock, et al., "Assessment of diagnostic quantitative fluorescent multiplex polymerase chain reaction assays performed on single cells", *Ann. Hum. Genet.* 62:9–23 (1998).

Axton, et al., "A Single–Tube Multiplex System for the Simultaneous Detection of 10Common Cystic Fibrosis Mutations", *Human Mutation*, 5:260–262 (1995).

Poyser et al., "Multiplex genotyping for cystic fibrosis from filter paper blood spots", *Ann. Clin. Biochem.*, 35:611–615 (1998).

Caudai, et al., "Detection of HCV and GBV–C/HGV injection by multiplex PCR in plasma samples of transfused subjects", *J. Virol Meth.*, 70: 79–83 (1998).

Songsivilai, et al., "Improved Amplification System for Detection of Hepatitis C virus Genome that Simultaneously Differentiates Viral Genotype", *Southeast Asian J. Trop. Med. Public Health*, 27(2): 237–243 (1996).

Oyofo, et al., "Detection of Enterotoxigenic *Eschericia coli*, Shigella and Campylobacter spp. by Multiplex PCR Assay", *J. Diarrhoeal Dis. Res.*, 14(3): 207–210 (1996).

L. Ripoll, et al., "Multiplex PCR–mediated Site–directed Mutagenesis for One–step Determination of Factor V Leiden and G20210A Transition of the Prothrombin Gene", pp. 960–961 (1997).

L. Ripoll, et al., "Multiplex ASA PCR for a Simultaneous Determination of Factor V Leiden Gene, G—A 20210 Prothrombin Gene and C—T 677 MTHFR Gene Mutations", *Thromb Haemost*, 79:1054–1055 (1998).

X. Xu et al., "Two Multiplex PCR–Based DNA Assays for the Thrombosis Risk Factors Prothrombin G20210A and Coagulation Factor V G1691A Polymorphisms", *Thrombosis Research* 93:265–269 (1999).

E. Gomez, et al., "Rapid Simultaneous Screening of Factor V Leiden and G20210A Prothrombin Variant by Multiplex Polymerase Chain Reaction on Whole Blood", *Blood* 91(6): 2208–2211 (1998).

D. Linfert, et al., "Rapid Multiplex Analysis for the Factor V Leiden and Prothrombin G20210A Mutations Associated with Hereditary Thrombophilia", Connecticut Medicine 62(9):519–525 (1998).

P. Nyren, et al., *Anal. Biochem.*, 244:367–373 (1997).

S. Borman, "Developers of Novel DNA Sequencers Claim Major Performance Advances", *C&EN*, pp. 37–40 (Jul. 24, 1995).

P. Belgrader, et al., "PCR Detection of Bacteria in Seven Minutes", *Science Magazine* 284:449–450 (1999).

K. Hayashi *Genetic Analysis: Techniques and Applications* 9:73–79 (1992).

Newton et al., *Nucl. Acids Res.*, 17:2503–2516 (1989).

Wu et al., *Proc. Natl. Acad. Sci., USA*, 86:2757–2760 (1989).

T. Nikiforov, et al., *Nucl. Acids Res.*, 22:4167–4175 (1994).

C. Wittwer, et al., *Biotechniques*, 22:130–138 (1997).

P. Holland, et al., *Proc. Natl. Acad. Sci., USA*, 88:7276–7280 (1991).

R. Kramer, et al., *Nat. Biotechnol.*, 14:303–308 (1996).

J. Shultz, D. Leippe, K. Lewis and M. Nelson, "Non–radioactive Measurement of DNA Using Coupled Enzymatic Reactions", Presentation Mar. 16–20, 1998 at a Parenteral Drug Association meeting in San Francisco, California.

* cited by examiner

Fig. 1

A  Wild Type Template

```
3' CTGAGCAGTACAGAGTCGAAATC 5' 10866(SEQ ID NO:2)
   TCTGACTCGTCATGTCTCAGCTTTAGTTTAATACGACTCACTATAG
                                              G
                                              G
   GTCTCTTCTGTTATATCAAG 5'   3'TCCACCTTAGTGTGACTC 10865(SEQ ID NO:1)
5' TTGCAGAGAAAGACAATATAGTTCTTGGAGAAGGTGGAATCACACTGAGTGGA 10870(SEQ ID NO:3)
                                    3' CCACTTCCACCTTAGTGTGACTC 5'
                                       10869(SEQ ID NO:5)
```

B  Mutant Template

```
3' CTGAGCAGTACAGAGTCGAAATC 5' 10866(SEQ ID NO:2)
   TCTGACTCGTCATGTCTCAGCTTTAGTTTAATACGACTCACTATAG
                                              G
                                              G
   GTCTCTTCTGTTATATCAAG 5'   3'TCCACCTTAGTGTGACTC 10865(SEQ ID NO:1)
5' TTGCAGAGAAAGACAATATAGTTCTTTGAGAAGGTGGAATCACACTGAGTGGA 10994(SEQ ID NO:4)
                                  3' ACACTTCCACCTTAGTGTGACTC 5' 10989(SEQ ID NO:6)
```

SEQUENCE LISTING

<160> NUMBER OF SEQ ID NOS: 69

<210> SEQ ID NO 1
<211> LENGTH: 89
<212> TYPE: DNA
<213> ORGANISM: Artificial Sequence
<220> FEATURE:
<223> OTHER INFORMATION: Description of Artificial Sequence:probe to wild-type targets 10870 and 10994

<400> SEQUENCE: 1
gaactatatt gtctttctct gattctgact cgtcatgtct cagctttagt ttaatacgac       60
tcactatagg gctcagtgtg attccacct                                         89

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence:probe which
      hybridizes to 10870 and 10994

<400> SEQUENCE: 2
ctaaagctga gacatgacga gtc                                               23

<210> SEQ ID NO 3
<211> LENGTH: 53
<212> TYPE: DNA
<213> ORGANISM: Artificial Sequence
<220> FEATURE:
<223> OTHER INFORMATION: Description of Artificial Sequence:wild-type
      target

<400> SEQUENCE: 3
ttgcagagaa agacaatata gttcttggag aaggtggaat cacactgagt gga              53

<210> SEQ ID NO 4
<211> LENGTH: 53
<212> TYPE: DNA
<213> ORGANISM: Artificial Sequence
<220> FEATURE:
<223> OTHER INFORMATION: Description of Artificial Sequence:mutant
      target

<400> SEQUENCE: 4
ttgcagagaa agacaatata gttctttgag aaggtggaat cacactgagt gga              53

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence:probe which
      hybridizes only to wild-type target

<400> SEQUENCE: 5
ctcagtgtga ttccacttca cc                                                22

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:probe which
      hybridizes only to mutant target

<400> SEQUENCE: 6
ctcagtgtga ttccaccttc aca                                               23

<210> SEQ ID NO 7
<211> LENGTH: 82
<212> TYPE: DNA
<213> ORGANISM: Artificial Sequence
<220> FEATURE:
<223> OTHER INFORMATION: Description of Artificial Sequence:circular probe

<400> SEQUENCE: 7
acaacgtcgt gactaggatc acgctaatgc ttcagcctga tgagtccgat cagcctgatg    60
agtccgatct ggccgtcgtt tt                                             82

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:wt target

<400> SEQUENCE: 8
cagtcacgac gttgtaaaac gacggccagt                                     30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:mutant
      target

<400> SEQUENCE: 9
cagtcacgac gttgtgaaac gacggccagt                                     30

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence:extension
      probe

<400> SEQUENCE: 10
agcattagcg tgatcc                                                    16

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence:
      complementary probe

<400> SEQUENCE: 11
cagcctgatg agtccg                                                    16

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:
      complementary to 11195 (wt) and 11194 (mutant) lacI

<400> SEQUENCE: 12
ttgtgccacg cggttgggaa tgta                                           24

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence:wild-type

```
      lacI

<400> SEQUENCE: 13
tacattccca accgcgtggc acaac                                              25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence:mutant lacI

<400> SEQUENCE: 14
tacattccca accgcgtggc acaat                                              25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence:
      complementary to 11193 (wt) and 11194 (mut) lacI

<400> SEQUENCE: 15
aactggcggg caaacagtcg ttgct                                              25

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence:wild-type
      lacI

<400> SEQUENCE: 16
agcaacgact gtttgcccgc cagttg                                             26

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence:mutant lacI

<400> SEQUENCE: 17
agcaacgact gtttgcccgc cagtta                                             26

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence:probe to
      wild-type lacI

<400> SEQUENCE: 18
tttgcccgcc agttgtt                                                       17

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence:probe to
      mutant lacI

<400> SEQUENCE: 19
```
tttgcccgcc agttatt                                                    17

<210> SEQ ID NO 20
<211> LENGTH: 51
<212> TYPE: DNA
<213> ORGANISM: Artificial Sequence
<220> FEATURE:
<223> OTHER INFORMATION: Description of Artificial Sequence:primer for
      Pst I restriction site

<400> SEQUENCE: 20
gcttaagctg caggcatat gtggtgatga tatcgtgggt gagttcattt a              51

<210> SEQ ID NO 21
<211> LENGTH: 51
<212> TYPE: DNA
<213> ORGANISM: Artificial Sequence
<220> FEATURE:
<223> OTHER INFORMATION: Description of Artificial Sequence:primer for
      Pst I restriction site

<400> SEQUENCE: 21
gcttaagctg caggccatg gtggtgatga tatcgtgggt gagttcattt t              51

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence:probe for
      oligo 53

<400> SEQUENCE: 22
ctggaaaatg aactcaccca cgatatcatc acca                                34

<210> SEQ ID NO 23
<211> LENGTH: 42
<212> TYPE: DNA
<213> ORGANISM: Artificial Sequence
<220> FEATURE:
<223> OTHER INFORMATION: Description of Artificial Sequence:probe for
      oligo 53

<400> SEQUENCE: 23
agcttggtga tgatatcgtg gtgagttca ttttccaggt ac                        42

<210> SEQ ID NO 24
<211> LENGTH: 34
<212> TYPE: DNA
<213> ORGANISM: Artificial Sequence
<220> FEATURE:
<223> OTHER INFORMATION: Description of Artificial Sequence:probe for
      oligo 53

<400> SEQUENCE: 24
ctggtaaatg aactcaccca cgatatcatc acca                                34

<210> SEQ ID NO 25
<211> LENGTH: 42
<212> TYPE: DNA
<213> ORGANISM: Artificial Sequence
<220> FEATURE:
<223> OTHER INFORMATION: Description of Artificial Sequence:probe for
      oligo 54

<400> SEQUENCE: 25

```
agcttggtga tgatatcgtg ggtgagttca tttaccaggt ac                        42
```

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence:contains
      Pst I restriction site

<400> SEQUENCE: 26

```
atgatgctgc agcaggaaac agctatgac                                       29
```

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence:contains
      Pst I restriction site

<400> SEQUENCE: 27

```
atgatgctgc aggttttccc agtcacgac                                       29
```

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence:probe to
      prothrombin pcr product, with phosphorothioate
      linkages between the first bases on the 5' end

<400> SEQUENCE: 28

```
atagcactgg gagcattgag gc                                              22
```

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:probe to
      prothrombin pcr product

<400> SEQUENCE: 29

```
gcacagacgg ctgttctctt                                                 20
```

<210> SEQ ID NO 30
<211> LENGTH: 22
<212> TYPE: DNA
<213> ORGANISM: Homo sapiens
<220> FEATURE:
<223> OTHER INFORMATION: Description of Artificial Sequence:probe for
      Factor V

<400> SEQUENCE: 30

```
tgcccagtgc ttaacaagac ca                                              22
```

<210> SEQ ID NO 31
<211> LENGTH: 20
<212> TYPE: DNA
<213> ORGANISM: Homo sapiens

<400> SEQUENCE: 31

```
tgttatcaca ctggtgctaa                                                 20
```

```
<210> SEQ ID NO 32
<211> LENGTH: 13
<212> TYPE: DNA
<213> ORGANISM: Homo sapiens

<400> SEQUENCE: 32
gtgattctca gca                                                        13

<210> SEQ ID NO 33
<211> LENGTH: 13
<212> TYPE: DNA
<213> ORGANISM: Homo sapiens

<400> SEQUENCE: 33
gtgattctca gcg                                                        13

<210> SEQ ID NO 34
<211> LENGTH: 22
<212> TYPE: DNA
<213> ORGANISM: Homo sapiens

<400> SEQUENCE: 34
gacaaaatac ctgtattcct cg                                              22

<210> SEQ ID NO 35
<211> LENGTH: 22
<212> TYPE: DNA
<213> ORGANISM: Homo sapiens

<400> SEQUENCE: 35
gacaaaatac ctgtattcct tg                                              22

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence:CAH reverse
      probe (CYP21 only)

<400> SEQUENCE: 36
ccagagcagg gagtagtctc                                                 20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence:CAH forward
      probe

<400> SEQUENCE: 37
gcatatagag catggctgtg                                                 20

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence:CAH forward
      probe (CYP21 only)

<400> SEQUENCE: 38
cctgtccttg ggagactac                                                  19
```

```
<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence:CAH reverse
      probe

<400> SEQUENCE: 39
cccagttcgt ggtctagc                                                    18

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence:CAH reverse
      probe

<400> SEQUENCE: 40
tcctcactca tccccaac                                                    18

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence:CAH forward
      probe

<400> SEQUENCE: 41
gaaatacgga cgtcccaagg c                                                21

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence:CAH reverse
      probe (CYP21 only)

<400> SEQUENCE: 42
ctttccagag cagggagtag                                                  20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence:CAH forward
      probe (CYP21 only)

<400> SEQUENCE: 43
ccggacctgt ccttgggaga                                                  20

<210> SEQ ID NO 44
<211> LENGTH: 40
<212> TYPE: DNA
<213> ORGANISM: Homo sapiens

<400> SEQUENCE: 44
agaagcccgg ggcaagaggc aggaggtgga ggctccggag                            40

<210> SEQ ID NO 45
<211> LENGTH: 40
<212> TYPE: DNA
<213> ORGANISM: Homo sapiens
```

```
<400> SEQUENCE: 45
agcttgtctg caggaggagc tgggggctgg agggtgggaa                               40

<210> SEQ ID NO 46
<211> LENGTH: 40
<212> TYPE: DNA
<213> ORGANISM: Homo sapiens

<400> SEQUENCE: 46
tccgaaggtg aggtaacagt tgatgctgca ggtgaggaga                               40

<210> SEQ ID NO 47
<211> LENGTH: 40
<212> TYPE: DNA
<213> ORGANISM: Homo sapiens

<400> SEQUENCE: 47
tccactgcag ccatgtgcaa gtgcccttcc aggagctgtc                               40

<210> SEQ ID NO 48
<211> LENGTH: 40
<212> TYPE: DNA
<213> ORGANISM: Homo sapiens

<400> SEQUENCE: 48
tcgtggtcta gctcctccta cagtcgctgc tgaatctggg                               40

<210> SEQ ID NO 49
<211> LENGTH: 40
<212> TYPE: DNA
<213> ORGANISM: Homo sapiens

<400> SEQUENCE: 49
gctaagggca caacgggcca caggcgcagc acctcggcga                               40

<210> SEQ ID NO 50
<211> LENGTH: 40
<212> TYPE: DNA
<213> ORGANISM: Homo sapiens

<400> SEQUENCE: 50
cagcttgtct gcaggaggag ttgggggctg gagggtggga                               40

<210> SEQ ID NO 51
<211> LENGTH: 40
<212> TYPE: DNA
<213> ORGANISM: Homo sapiens

<400> SEQUENCE: 51
ggctaagggc acaacgggcc gcaggcgcag cacctcggcg                               40

<210> SEQ ID NO 52
<211> LENGTH: 18
<212> TYPE: DNA
<213> ORGANISM: Homo sapiens

<400> SEQUENCE: 52
cggagcctcc acctcccg                                                      18

<210> SEQ ID NO 53
<211> LENGTH: 18
<212> TYPE: DNA
```

```
<213> ORGANISM: Homo sapiens

<400> SEQUENCE: 53
caccctccag cccccagc                                                 18

<210> SEQ ID NO 54
<211> LENGTH: 18
<212> TYPE: DNA
<213> ORGANISM: Homo sapiens

<400> SEQUENCE: 54
cggagcctcc acctcctg                                                 18

<210> SEQ ID NO 55
<211> LENGTH: 19
<212> TYPE: DNA
<213> ORGANISM: Homo sapiens

<400> SEQUENCE: 55
cctcacctgc agcatcaac                                                19

<210> SEQ ID NO 56
<211> LENGTH: 18
<212> TYPE: DNA
<213> ORGANISM: Homo sapiens

<400> SEQUENCE: 56
caccctccag cccccaac                                                 18

<210> SEQ ID NO 57
<211> LENGTH: 15
<212> TYPE: DNA
<213> ORGANISM: Homo sapiens

<400> SEQUENCE: 57
cctggaaggg cactt                                                    15

<210> SEQ ID NO 58
<211> LENGTH: 19
<212> TYPE: DNA
<213> ORGANISM: Homo sapiens

<400> SEQUENCE: 58
cctcacctgc agcatcatc                                                19

<210> SEQ ID NO 59
<211> LENGTH: 15
<212> TYPE: DNA
<213> ORGANISM: Homo sapiens

<400> SEQUENCE: 59
cctggaaggg cacgt                                                    15

<210> SEQ ID NO 60
<211> LENGTH: 18
<212> TYPE: DNA
<213> ORGANISM: Homo sapiens

<400> SEQUENCE: 60
gattcagcag cgactgta                                                 18

<210> SEQ ID NO 61
<211> LENGTH: 18
```

```
<212> TYPE: DNA
<213> ORGANISM: Homo sapiens

<400> SEQUENCE: 61
gattcagcag cgactgca                                                  18

<210> SEQ ID NO 62
<211> LENGTH: 18
<212> TYPE: DNA
<213> ORGANISM: Homo sapiens

<400> SEQUENCE: 62
cgaggtgctg cgcctgcg                                                  18

<210> SEQ ID NO 63
<211> LENGTH: 18
<212> TYPE: DNA
<213> ORGANISM: Homo sapiens

<400> SEQUENCE: 63
cgaggtgctg cgcctgtg                                                  18

<210> SEQ ID NO 64
<211> LENGTH: 20
<212> TYPE: DNA
<213> ORGANISM: Homo sapiens

<400> SEQUENCE: 64
gggatcacat cgtggagatg                                                20

<210> SEQ ID NO 65
<211> LENGTH: 20
<212> TYPE: DNA
<213> ORGANISM: Homo sapiens

<400> SEQUENCE: 65
gggatcacaa cgaggagaag                                                20

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: probe for
      Rice Genome (with phosphorothoiate linkages)

<400> SEQUENCE: 66
cccaacacct tacagaaatt agc                                            23

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: probe for
      Rice genome

<400> SEQUENCE: 67
tctcaagaca caaataactg cag                                            23

<210> SEQ ID NO 68
<211> LENGTH: 15
<212> TYPE: DNA
<213> ORGANISM: Artificial Sequence
<220> FEATURE:
```

-continued

```
<223> OTHER INFORMATION: Description of Artificial Sequence: probe
      for "G" allele of Rice

<400> SEQUENCE: 68
agaacatctg caagg                                                    15

<210> SEQ ID NO 69
<211> LENGTH: 15
<212> TYPE: DNA
<213> ORGANISM: Artificial Sequence
<220> FEATURE:
<223> OTHER INFORMATION: Description of Artificial Sequence:probe for
      "T" allele of Rice

<400> SEQUENCE: 69
agaacatctg caagt                                                    15
```

US 6,277,578 B1

DEPLOYMERIZATION METHOD FOR NUCLEIC ACID DETECTION OF AN AMPLIFIED NUCLEIC ACID TARGET

CROSS-REFERENCE TO RELATED APPLICATIONS

This application is a continuation-in-part of U.S. Ser. No. 09/358,972, filed on Jul. 21, 1999, which is a continuation-in-part of U.S. Ser. No. 09/252,436, filed on Feb. 18, 1999, U.S. Pat. No. 6,159,693 which is a continuation-in-part of U.S. Ser. No. 09/042,287, filed Mar. 13, 1998, all of which are incorporated herein by reference.

TECHNICAL FIELD

The invention relates to nucleic acid detection. More specifically, the invention relates to detection of amplified, targeted, predetermined nucleic acid sequences in nucleic acid target/probe hybrids, and the various applications of target nucleic acid amplification.

BACKGROUND OF THE INVENTION

Several methods of amplification coupled with detection of the presence or absence of a nucleic acid target sequence are currently used in the art. The amplification of a nucleic acid target that is present at a low concentration within a nucleic acid sample is useful for enhancing the sensitivity of a detection method. Known amplification methods include, inter alia, polymerase chain reaction, ligase chain reaction, repair chain reaction, amplification of transcripts, self-sustained sequence replication (3SR), ligation activated transcription (LAT), strand displacement amplification (SDA) and rolling circle replication. These processes are discussed in greater detail in the "Detailed Description of the Invention".

There are several ways to use nucleic acid amplification methods in a nucleic acid detection method. One approach is to make the amplification primers complementary to the nucleic acid target. Then the presence of an amplification product is indicative of the presence of the nucleic acid target. In another approach, amplification primers are used to amplify a region of nucleic acid that contains a nucleic acid target. Then, another method is used to detect the presence of the nucleic acid target sequence within the amplification product.

Hybridization methods to detect nucleic acids are dependent upon knowledge of the nucleic acid sequence. Many known nucleic acid detection techniques depend upon specific nucleic acid hybridization in which an oligonucleotide probe is hybridized or annealed to nucleic acid in the sample or on a blot, and the hybridized probes are detected.

A traditional type of process for the detection of hybridized nucleic acid uses labeled nucleic acid probes to hybridize to a nucleic acid sample. For example, in a Southern blot technique, a nucleic acid sample is separated in an agarose gel based on size and affixed to a membrane, denatured, and exposed to the labeled nucleic acid probe under hybridizing conditions. If the labeled nucleic acid probe forms a hybrid with the nucleic acid on the blot, the label is bound to the membrane. Probes used in Southern blots have been labeled with radioactivity, fluorescent dyes, digoxygenin, horseradish peroxidase, alkaline phosphatase and acridinium esters.

Another type of process for the detection of hybridized nucleic acid takes advantage of the polymerase chain reaction (PCR). The PCR process is well known in the art (U.S. Pat. Nos. 4,683,195, 4,683,202, and 4,800,159). To briefly summarize PCR, nucleic acid primers, complementary to opposite strands of a nucleic acid amplification target sequence, are permitted to anneal to the denatured sample. A DNA polymerase (typically heat stable) extends the DNA duplex from the hybridized primer. The process is repeated to amplify the nucleic acid target. If the nucleic acid primers do not hybridize to the sample, then there is no corresponding amplified PCR product. In this case, the PCR primer acts as a hybridization probe. PCR-based methods are of limited use for the detection of nucleic acid of unknown sequence.

In a PCR method, the amplified nucleic acid product may be detected in a number of ways, e.g. incorporation of a labeled nucleotide into the amplified strand by using labeled primers. Primers used in PCR have been labeled with radioactivity, fluorescent dyes, digoxygenin, horseradish peroxidase, alkaline phosphatase, acridinium esters, biotin and jack bean urease. PCR products made with unlabeled primers may be detected in other ways, such as electrophoretic gel separation followed by dye-based visualization.

Fluorescence techniques are also known for the detection of nucleic acid hybrids. U.S. Pat. No. 5,691,146 describes the use of fluorescent hybridization probes that are fluorescence-quenched unless they are hybridized to the target nucleic acid sequence. U.S. Pat. No. 5,723,591 describes fluorescent hybridization probes that are fluorescence-quenched until hybridized to the target nucleic acid sequence, or until the probe is digested. Such techniques provide information about hybridization, and are of varying degrees of usefulness for the determination of single base variances in sequences. Some fluorescence techniques involve digestion of a nucleic acid hybrid in a 5' to 3' direction to release a fluorescent signal from proximity to a fluorescence quencher, for example, TaqMan® (Perkin Elmer; U.S. Pat. Nos. 5,691,146 and 5,876,930).

Enzymes having template-specific polymerase activity for which some 3' to 5' depolymerization activity has been reported include E. coli DNA Polymerase (Deutscher and Kornberg, J. Biol. Chem., 244(11):3019–28 (1969)), T7 DNA Polymerase (Wong et al., Biochemistry 30:526–37 (1991); Tabor and Richardson, J. Biol. Chem. 265: 8322–28 (1990)), E. coli RNA polymerase (Rozovskaya et al., Biochem. J. 224:645–50 (1994)), AMV and RLV reverse transcriptases (Srivastava and Modak, J. Biol. Chem. 255: 2000–4 (1980)), and HIV reverse transcriptase (Zinnen et al., J. Biol. Chem. 269:24195–202 (1994)). A template-dependent polymerase for which 3' to 5' exonuclease activity has been reported on a mismatched end of a DNA hybrid is phage 29 DNA polymerase (de Vega, M. et al. EMBO J., 15:1182–1192, 1996).

A variety of methodologies currently exist for the detection of single nucleotide polymorphisms (SNPs) that are present in genomic DNA. SNPs are DNA point mutations or insertions/deletions that are present at measurable frequencies in the population. SNPs are the most common variations in the genome. SNPs occur at defined positions within genomes and can be used for gene mapping, defining population structure, and performing functional studies. SNPs are useful as markers because many known genetic diseases are caused by point mutations and insertions/deletions.

In rare cases where a SNP alters a fortuitous restriction enzyme recognition sequence, differential sensitivity of the amplified DNA to cleavage can be used for SNP detection. This technique requires that an appropriate restriction enzyme site be present or introduced in the appropriate sequence context for differential recognition by the restriction endonuclease. After amplification, the products are cleaved by the appropriate restriction endonuclease and products are analyzed by gel electrophoresis and subsequent staining. The throughput of analysis by this technique is limited because samples require processing, gel analysis, and significant interpretation of data before SNPs can be accurately determined.

Single strand conformational polymorphism (SSCP) is a second technique that can detect SNPs present in an amplified DNA segment (Hayashi, K. *Genetic Analysis: Techniques and Applications* 9:73–79, 1992). In this method, the double stranded amplified product is denatured and then both strands are allowed to reanneal during electrophoresis in non-denaturing polyacrylamide gels. The separated strands assume a specific folded conformation based on intramolecular base pairing. The electrophoretic properties of each strand are dependent on the folded conformation. The presence of single nucleotide changes in the sequence can cause a detectable change in the conformation and electrophoretic migration of an amplified sample relative to wild type samples, allowing SNPs to be identified. In addition to the limited throughput possible by gel-based techniques, the design and interpretation of SSCP based experiments can be difficult. Multiplex analysis of several samples in the same SSCP reaction is extremely challenging. The sensitivity required in mutation detection and analysis has led most investigators to use radioactively labeled PCR products for this technique.

In a process to amplify and detect single nucleotide polymorphisms using an amplification refractory mutation system (ARMS, also known as allele specific PCR or ASPCR), two amplification reactions are used to determine if a SNP is present in a DNA sample (Newton et al. *Nucl Acids Res* 17:2503, 1989; Wu et al. *PNAS* 86:2757, 1989). Both amplification reactions contain a common primer for the target of interest. The first reaction contains a second primer specific for the wild type product which will give rise to a PCR product if the wild type gene is present in the sample. The second PCR reaction contains a primer that has a single nucleotide change at or near the 3' end that represents the base change that is present in the mutated form of the DNA. The second primer, in conjunction with the common primer, will only function in PCR if genomic DNA that contains the mutated form of genomic DNA is present. This technique requires duplicate amplification reactions to be performed and analyzed by gel electrophoresis to ascertain if a mutated form of a gene is present. In addition, the data must be manually interpreted.

Single base extension (GBA®) is a technique that allows the detection of SNPs by hybridizing a single strand DNA probe to a captured DNA target (Nikiforov, T. et al. *Nucl Acids Res* 22:4167–4175). Once hybridized, the single-stranded probe is extended by a single base with labeled dideoxynucleotides. The labeled, extended products are then detected using calorimetric or fluorescent methodologies.

A variety of technologies related to real-time (or kinetic) PCR have been adapted to perform SNP detection. Many of these systems are platform based, and require specialized equipment, complicated primer design, and expensive supporting materials for SNP detection. In contrast, the process of this invention has been designed as a modular technology that can use a variety of instruments that are suited to the throughput needs of the end-user. In addition, the coupling of luciferase detection sensitivity with standard oligonucleotide chemistry and well-established enzymology provides a flexible and open system architecture. Alternative analytical detection methods, such as mass spectroscopy, HPLC, and fluorescence detection methods can also be used in the process of this invention, providing additional assay flexibility.

SNP detection using real-time amplification relies on the ability to detect amplified segments of nucleic acid as they are during the amplification reaction. Three basic real-time SNP detection methodologies exist: (i) increased fluorescence of double strand DNA specific dye binding, (ii) decreased quenching of fluorescence during amplification, and (iii) increased fluorescence energy transfer during amplification (Wittwer, C. et al. *Biotechniques* 22:130–138, 1997). All of these techniques are non-gel based and each strategy will be briefly discussed.

A variety of dyes are known to exhibit increased fluorescence in response to binding double stranded DNA. This property is utilized in conjunction with the amplification refractory mutation system described above to detect the presence of SNP. Production of wild type or mutation containing PCR products are continuously monitored by the increased fluorescence of dyes such as ethidium bromide or SYBER Green as they bind to the accumulating PCR product. Note that dye binding is not selective for the sequence of the PCR product, and high non-specific background can give rise to false signals with this technique.

A second detection technology for real time PCR, known generally as exonuclease primers (TaqMan® probes), utilizes the 5' exonuclease activity of thermostable polymerases such as Taq to cleave dual-labeled probes present in the amplification reaction (Wittwer, C. et al. *Biotechniques* 22:130–138, 1997; Holland, P et al *PNAS* 88:7276–7280, 1991). While complementary to the PCR product, the probes used in this assay are distinct from the PCR primer and are dually-labeled with both a molecule capable of fluorescence and a molecule capable of quenching fluorescence. When the probes are intact, intramolecular quenching of the fluorescent signal within the DNA probe leads to little signal. When the fluorescent molecule is liberated by the exonuclease activity of Taq during amplification, the quenching is greatly reduced leading to increased fluorescent signal.

An additional form of real-time PCR also capitalizes on the intramolecular quenching of a fluorescent molecule by use of a tethered quenching moiety. This molecular beacon technology utilizes hairpin-shaped molecules with an internally-quenched fluorophore whose fluorescence is restored by binding to a DNA target of interest (Kramer, R. et al. *Nat. Biotechnol.* 14:303–308, 1996). Increased binding of the molecular beacon probe to the accumulating PCR product can be used to specifically detect SNPs present in genomic DNA.

A final, general fluorescent detection strategy used for detection of SNP in real time utilizes synthetic DNA segments known as hybridization probes in conjunction with a process known as fluorescence resonance energy transfer (FRET) (Wittwer, C. et al. Biotechniques 22:130–138, 1997; Bernard, P. et al. *Am. J. Pathol.* 153:1055–1061, 1998). This technique relies on the independent binding of labeled DNA probes on the target sequence. The close approximation of the two probes on the target sequence increases resonance energy transfer from one probe to the other, leading to a unique fluorescence signal. Mismatches caused by SNPs that disrupt the binding of either of the probes can be used to detect mutant sequences present in a DNA sample.

There is a need for highly sensitive, diagnostic applications that are capable of determining the number of specific nucleic acid molecules in a sample, e.g. virus molecules present in a body sample ("viral load"). For example, the presence of viral particles in the circulation system or in specific tissues is a means of monitoring the severity of viral infection. Several methods are currently used in the art for determining viral load. U.S. Pat. No. 5,667,964 discloses a method for the determination of the number of HIV-1 infected patient cells using reactive oxygen-intermediate generators. U.S. Pat. No. 5,389,512 discloses a method for determining the relative amount of a viral nucleic acid segment in a sample using PCR.

G. Garinis et al., *J. Clin. Lab. Anal.* 13:122–5 (1999) compare the determination of viral load results using an enzyme-linked immunosorbant assay (ELISA), a recombinant immunoblot assay (RIBA), and a reverse transcriptase polymerase chain reaction method (RT-PCR) in the detection of hepatitis C virus (HCV) infection in haemodialysis patients. The quantitative hepatitis HCV RT-PCR assay had a detection level of about 2,000 viral copies/mL serum. Holguin et al., *Eur. J. Clin. Microbiol. Infect. Dis.* 18:256–9 (1999) compare plasma HIV-1 RNA levels using several commercially available assays, namely the second-generation HIV-1 branched DNA assay, the Nuclisens assay, the Amplicor® Monitor reverse transcriptase polymerase chain reaction assay, and the Ultradirect Monitor. There is a demand for methods to quantitatively determine the presence or absence of a nucleic acid target when the quantities of nucleic acid target sequence in the sample is very low.

In summary, known amplification methods provide an enhanced amount of nucleic acid that can be used for a desired nucleic acid hybrid detection assay to determine whether a desired nucleic acid sequence is present or absent. However, each nucleic acid sample must be cycled multiple times to provide a sufficient amount of nucleic acid for analysis. Each cycle takes additional time and reagents. In addition, each additional cycle for some of the cycling methods increases the risk of a mutation being introduced into the resulting amplified DNA.

It would be beneficial if the number of cycles could be minimized so that time taken and reagents used could be minimized. It would also be beneficial if the number of cycles could be minimized in order to, in turn, minimize the opportunity for mutation(s) to be introduced into the resulting amplified DNA. In addition, the greater number of cycles that are carried out, the greater is the opportunity for an error to be made or for some other mishap to occur, for example, an equipment malfunction.

It would therefore be beneficial if a highly sensitive nucleic acid hybrid detection method was available that would provide accurate results using a minimal number of amplification cycles. It would also be beneficial if a highly sensitive nucleic acid hybrid detection method was available that was flexible and could be used in conjunction with a variety of amplification methods.

The disclosure that follows provides one such sensitive and accurate method for determining the presence or absence of a predetermined nucleic acid sequence in a sample that is assayed following a minimal number of amplification cycles.

BRIEF SUMMARY OF THE INVENTION

The present invention contemplates an improved nucleic acid assay method wherein the presence or absence of a predetermined nucleic acid target sequence in a sample is determined, and a nucleic acid target-containing sequence in a nucleic acid sample to be assayed is amplified to form an amplified nucleic acid sample prior to the determination. The improvement is that the presence or absence of the predetermined nucleic acid target sequence is determined by the following steps.

First, the amplified nucleic acid sample to be assayed is admixed with one or more nucleic acid probes to form a hybridization composition. The 3'-terminal region of the nucleic acid probes (i) hybridizes with partial or total complementarity to at least one predetermined nucleic acid target sequence when that sequence is present in the sample and (ii) includes an identifier nucleotide.

Second, the hybridization composition is maintained for a time period sufficient to form a treated sample that may contain the amplified predetermined nucleic acid target sequence hybridized with a nucleic acid probe.

Third, the treated sample is admixed with a depolymerizing amount of an enzyme whose activity is to release one or more nucleotides from the 3'-terminus of a hybridized nucleic acid probe to form a treated reaction mixture.

Fourth, the treated reaction mixture is maintained for a time period sufficient to permit the enzyme to depolymerize hybridized nucleic acid and release identifier nucleotides therefrom.

Finally, the presence of released identifier nucleotides is analyzed to obtain an analytical output, the analytical output indicating the presence or absence of at least one nucleic acid target sequence in the nucleic acid sample.

Preferably, the identifier nucleotide is a nucleoside triphosphate. Most preferably a nucleoside diphosphate kinase transfers a phosphate from the nucleoside triphosphate to convert ADP to ATP. Preferably, the nucleoside diphosphate kinase activity is provided by a protein encoded by a nucleic acid having a sequence that comprises the nucleic acid sequence of a nucleoside diphosphate kinase that is encoded by *Pyrococcus furiosus*. Preferably, the analytical output is obtained by luminescence spectroscopy, or by fluorescence spectroscopy, or by mass spectrometry, or by absorbance spectroscopy. The label may be included at any position in the hybrid, but preferably, the released identifier nucleotide includes a label or the identifier nucleotide is labeled after release from said hybrid. Preferably the label results in a fluorescent output.

In one aspect, the nucleic acid sample is amplified by rolling circle amplification. In another aspect, the nucleic acid sample is amplified by PCR amplification. In a further aspect, the nucleic acid sample is amplified by ligase chain reaction amplification.

In one particular contemplated amplification and interrogation process of the invention that incorporates ligase chain reaction or repair chain reaction techniques, the presence or absence of a predetermined nucleic acid target sequence is determined, with the following steps. A ligation reaction solution is provided, comprising a ligating amount of a ligase, a nucleic acid sample and an open circle probe. The nucleic acid sample may contain the predetermined nucleic acid target sequence. The nucleic acid target sequence has a 3'- portion and a 5'-portion. The open circle probe comprises an open circle probe 3'-terminal region, a linker region, and an open circle probe 5'-terminal region. The open circle probe further comprises a detection primer target and an amplification primer target. The amplification primer target is downstream of the detection primer target.

Upon hybridization between the open circle probe and the predetermined nucleic acid target sequence, the open circle probe 3'-terminal region is complementary to a sequence of the 3' portion of the nucleic acid target sequence. Similarly, the open circle probe 5'-terminal region is complementary to a sequence of the 5' portion of the nucleic acid target sequence.

The ligation reaction solution optionally further comprises a polymerizing amount of a DNA polymerase and deoxynucleoside triphosphates. Preferably, this is when the hybridized open circle probe 3'-terminus is not adjacent and ligatable to the hybridized open circle probe 5'-terminus and a gap is present between those termini.

The ligation reaction solution is maintained for a time period sufficient to permit the filling-in of the gap when DNA polymerase is present, and also for a time period sufficient for ligation of the termini of the open circle probe to form a closed circular probe, and thus a treated ligation reaction solution.

The closed circular probe is admixed with an amplification primer, which hybridizes with the amplification primer target, nucleoside triphosphates, and a polymerizing amount of a DNA polymerase to form a replication reaction mixture. The replication reaction mixture is maintained for a time period sufficient to permit the extension of a nucleic acid strand from the amplification primer. The extension product nucleic acid strand comprises an interrogation target to form a treated replication mixture.

An interrogation probe is admixed with the treated replication mixture. The interrogation probe is complementary to the target, and comprises an identifier nucleotide in its $3^1$-terminal region. The treated replication mixture is denatured before, during or after addition of the probe to form a denatured mixture. Preferably, the treated replication mixture is denatured after addition of the probe. The denatured mixture is annealed to permit the formation of a hybrid between the interrogation probe and the interrogation target, when present, thus forming an interrogation solution. A depolymerizing amount of an enzyme, whose activity is to release one or more nucleotides from the 3'-terminus of a hybridized nucleic acid probe, is admixed with the interrogation solution, thus forming a depolymerization reaction mixture. The depolymerization and analysis for released identifier nucleotide is as described above.

Preferably, the depolymerizing enzyme is thermostable. In a preferred embodiment, the free nucleotide triphosphates are separated from the treated replication mixture prior to the depolymerization step.

Optionally, in the above process wherein there is a gap present between the termini of the hybridized open circle probe, the portion of the predetermined nucleic acid target sequence between the 3'- and 5'-termini of the hybridized open circle probe that is opposite the gap contains three or fewer nucleotides and only nucleoside triphosphates complementary to the three or fewer nucleotides are present in the ligation reaction solution. Preferably, a polymerizing amount of a DNA polymerase and nucleoside triphosphates are present in the ligation reaction solution. Optionally, the open circle probe comprises a plurality of detection primer targets. Preferably, in the above process, the presence or absence of a plurality of predetermined nucleic acid targets is determined using a plurality of detection probes comprising different identifier nucleotides. Analysis of the released identifier nucleotide is preferably done according to methods disclosed elsewhere herein.

Another embodiment of the invention that incorporates rolling circle replication techniques contemplates an amplification and interrogation process to determine the presence or absence of a predetermined nucleic acid target sequence having a 3'-portion and a 5'-portion comprising the following steps.

A ligation reaction solution is provided, comprising (i) a ligating amount of a ligase, (ii) a nucleic acid sample that may contain a predetermined nucleic acid target sequence wherein the nucleic acid target sequence has a 3'-portion and a 5'-portion, (iii) a pair of ligation probes, the ligation probe further including a detection primer target and an amplification primer target, the amplification primer target being downstream of the detection primer target, wherein upon hybridization between the open circle probe and the nucleic acid target sequence, the open circle probe 3'-terminal region is complementary to a sequence of the 3'-portion of the predetermined nucleic acid target sequence, and the open circle probe 5'-terminal region is complementary to a sequence of the 5'-portion of said predetermined nucleic acid target sequence, and (iv) optionally further comprising a polymerizing amount of a DNA polymerase and deoxynucleoside triphosphates when the hybridized open circle probe 3'-terminus is not adjacent and ligatable to the hybridized open circle probe 5'-terminus and a gap is present between those termini.

The ligation reaction solution is maintained for a time period sufficient to permit filling-in of the gap, when present, and ligation of the termini of the open circle probe to form a closed circular probe and a treated ligation reaction solution.

The closed circular probe is admixed with an amplification primer that hybridizes with the amplification primer target, nucleoside triphosphates, and a polymerizing amount of a DNA polymerase to form a replication reaction mixture.

The replication reaction mixture is maintained for a time period sufficient to permit extension of a nucleic acid strand from the amplification primer, wherein the extension product nucleic acid strand comprises a interrogation target to form a treated replication mixture.

An interrogation probe is admixed with the treated replication mixture, wherein the interrogation probe is complementary to the interrogation target and comprises an identifier nucleotide in the 3'-terminal region.

The treated replication mixture is denatured to form a denatured mixture.

The denatured mixture is annealed to form a hybrid between the interrogation probe and the interrogation target when present to form an interrogation solution.

A depolymerizing amount of an enzyme whose activity is to release one or more nucleotides from the 3'-terminus of a hybridized nucleic acid probe is admixed with the interrogation solution to form a depolymerization reaction mixture.

The depolymerization reaction mixture is maintained under depolymerizing conditions for a time period sufficient to permit the enzyme to depolymerize hybridized nucleic acid and release identifier nucleotide therefrom. The presence of released identifier nucleotide is analyzed to obtain an analytical output, the analytical output indicating the presence or absence of the predetermined nucleic acid target sequence.

Preferably, the depolymerizing enzyme is thermostable. In one embodiment of the process, free nucleotide triphosphates are separated from the treated replication mixture prior to step admixing a depolymerizing amount of an enzyme whose activity is to release one or more nucleotides from the 3'-terminus of a hybridized nucleic acid probe with the interrogation solution to form a depolymerization reaction mixture. In another embodiment of the process, there is a gap present between the termini of the hybridized open circle probe, the portion of the predetermined nucleic acid target sequence between the 3'- and 5'-termini of the hybridized open circle probe that is opposite the gap contains three or fewer nucleotides and only nucleoside triphosphates complementary to the three or fewer nucleotides are present in the ligation reaction solution. Preferably, a polymerizing amount of a DNA polymerase and nucleoside triphosphates are present in the ligation reaction solution.

Optionally, the open circle probe comprises a plurality of detection primer targets. Preferably, the presence or absence of a plurality of predetermined nucleic acid targets is determined using a plurality of distinguishable detection probes, for example probes having differently labeled identifier nucleotides.

Another embodiment of the invention is a method for determining the presence or absence of a restriction endonuclease recognition sequence in a nucleic acid sample that comprises the following steps. A treated sample is provided that may contain a hybridized nucleic acid target that is a cleaved restriction endonuclease recognition sequence that includes an identifier nucleotide in the restriction endonuclease recognition sequence. The treated sample is admixed with a depolymerizing amount of an enzyme whose activity is to release one or more nucleotides from the 3'-terminus of a restriction endonuclease recognition sequence to form a treated reaction mixture. The treated reaction mixture is maintained for a time period sufficient to permit the enzyme to depolymerize hybridized nucleic acid and release identifier nucleotide therefrom. The presence of released identifier nucleotide is analyzed for to obtain an analytical output, the analytical output indicating the presence or absence of said restriction endonuclease recognition sequence.

In one embodiment, the above process includes the further steps of forming a treated sample by providing an endonuclease cleavage reaction solution comprising a nucleic acid sample and a restriction endonuclease enzyme specific for the restriction endonuclease recognition sequence, and maintaining the endonuclease cleavage reaction solution for a time period sufficient for the restriction endonuclease enzyme to cleave the restriction endonuclease recognition sequence to form a treated sample. In some embodiments, the process includes the further step of amplifying a nucleic acid target sequence in a nucleic acid sample to provide said restriction endonuclease recognition sequence.

In some embodiments, the nucleic acid target sequence in the sample is amplified by the following further steps. A crude nucleic acid sample is admixed with PCR amplification primers that are complementary to regions upstream and downstream of the nucleic acid target sequence and a template-dependent polymerase to form an amplification sample mixture wherein either the nucleic acid target sequence or the PCR amplification primers includes a restriction endonuclease recognition sequence. The amplification sample mixture is maintained for a time period sufficient to denature the nucleic acid target sequence to form a denatured amplification reaction mixture, and the denatured amplification reaction mixture is annealed for a time period sufficient for PCR amplification primers to anneal to the nucleic acid target sequence to form an amplification reaction mixture. The amplification reaction mixture is maintained for a time period sufficient to permit the template-dependent polymerase to extend the nucleic acid from the PCR primers to form an amplified nucleic acid sample.

Definitions

To facilitate understanding of the invention, a number of terms are defined below.

"Nucleoside", as used herein, refers to a compound consisting of a purine [guanine (G) or adenine (A)] or pyrimidine [thymine (T), uridine (U) or cytidine (C)] base covalently linked to a pentose, whereas "nucleotide" refers to a nucleoside phosphorylated at one of its pentose hydroxyl groups. "XTP", "XDP" and "XMP" are generic designations for ribonucleotides and deoxyribonucleotides, wherein the "TP" stands for triphosphate, "DP" stands for diphosphate, and "MP" stands for monophosphate, in conformity with standard usage in the art. Subgeneric designations for ribonucleotides are "NMP", "NDP" or "NTP", and subgeneric designations for deoxyribonucleotides are "dNMP", "dNDP" or "dNTP". Also included as "nucleoside", as used herein, are materials that are commonly used as substitutes for the nucleosides above such as modified forms of these bases (e.g. methyl guanine) or synthetic materials well known in such uses in the art, such as inosine.

A "nucleic acid", as used herein, is a covalently linked sequence of nucleotides in which the 3' position of the pentose of one nucleotide is joined by a phosphodiester group to the 5' position of the pentose of the next, and in which the nucleotide residues (bases) are linked in specific sequence; i.e., a linear order of nucleotides. A "polynucleotide", as used herein, is a nucleic acid containing a sequence that is greater than about 100 nucleotides in length. An "oligonucleotide", as used herein, is a short polynucleotide or a portion of a polynucleotide. An oligonucleotide typically contains a sequence of about two to about one hundred bases. The word "oligo" is sometimes used in place of the word "oligonucleotide".

A base "position" as used herein refers to the location of a given base or nucleotide residue within a nucleic acid.

A "nucleic acid of interest", as used herein, is any particular nucleic acid one desires to study in a sample.

The term "isolated" when used in relation to a nucleic acid or protein, refers to a nucleic acid sequence or protein that is identified and separated from at least one contaminant (nucleic acid or protein, respectively) with which it is ordinarily associated in its natural source. Isolated nucleic acid or protein is present in a form or setting that is different from that in which it is found in nature. In contrast, non-isolated nucleic acids or proteins are found in the state they exist in nature.

As used herein, the term "purified" or "to purify" means the result of any process which removes some contaminants from the component of interest, such as a protein or nucleic acid. The percent of a purified component is thereby increased in the sample.

The term "wild-type", as used herein, refers to a gene or gene product that has the characteristics of that gene or gene product that is most frequently observed in a population and is thus arbitrarily designated the "normal" or "wild-type" form of the gene. In contrast, the term "modified" or "mutant" as used herein, refers to a gene or gene product that displays modifications in sequence and/or functional properties (i.e., altered characteristics) when compared to the wild-type gene or gene product.

Nucleic acids are known to contain different types of mutations. As used herein, a "point" mutation refers to an alteration in the sequence of a nucleotide at a single base position. A "lesion", as used herein, refers to site within a nucleic acid where one or more bases are mutated by deletion or insertion, so that the nucleic acid sequence differs from the wild-type sequence.

A "single nucleotide polymorphism" or SNP, as used herein, is a DNA point mutation or insertion/deletion that is present at a measurable frequency in a population. SNPs are the most common variations in the genome. SNPs occur at defined positions within genomes and can be used for gene mapping, defining population structure, and performing functional studies. SNPs are useful as markers because many known genetic diseases are caused by point mutations and insertions/deletions.

Homologous genes or alleles from different species are also known to vary in sequence. Regions of homologous genes or alleles from different species can be essentially identical in sequence. Such regions are referred to herein as "regions of identity". It is contemplated herein that a "region of substantial identity" can contain some "mismatches", where bases at the same position in the region of identity are different. This base position is referred to herein as "mismatch position".

DNA molecules are said to have a "5'-terminus" (5' end) and a "3'-terminus" (3' end) because nucleic acid phosphodiester linkages occur to the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus. As used herein, a nucleic acid sequence, even if internal to a larger oligonucleotide or polynucleotide, also can be said to have 5'- and 3'- ends. For example, a gene sequence located within a larger chromosome sequence can still be said to have a 5'- and 3'-end.

As used herein, the 3'-terminal region of the nucleic acid probe refers to the region of the probe including nucleotides within about 10 residues from the 3'-terminal position.

In either a linear or circular DNA molecule, discrete elements are referred to as being "upstream" or "5'" relative to an element if they are bonded or would be bonded to the 5'-end of that element. Similarly, discrete elements are "downstream" or "3'" relative to an element if they are or would be bonded to the 3'-end of that element. Transcription proceeds in a 5' to 3' manner along the DNA strand. This means that RNA is made by the sequential addition of ribonucleotide-5'-triphosphates to the 3'-terminus of the growing chain (with the elimination of pyrophosphate).

As used herein, the term "target nucleic acid" or "nucleic acid target" refers to a particular nucleic acid sequence of interest. Thus, the "target" can exist in the presence of other nucleic acid molecules or within a larger nucleic acid molecule.

As used herein, the term "nucleic acid probe" refers to an oligonucleotide or polynucleotide that is capable of hybridizing to another nucleic acid of interest. A nucleic acid probe may occur naturally as in a purified restriction digest or be produced synthetically, recombinantly or by PCR amplification. As used herein, the term "nucleic acid probe" refers to the oligonucleotide or polynucleotide used in a method of the present invention. That same oligonucleotide could also be used, for example, in a PCR method as a primer for polymerization, but as used herein, that oligonucleotide would then be referred to as a "primer". Herein, oligonucleotides or polynucleotides can contain a modified linkage such as a phosphorothioate bond.

As used herein, the terms "complementary" or "complementarity" are used in reference to nucleic acids (i.e., a sequence of nucleotides) related by the well-known basepairing rules that A pairs with T and C pairs with G. For example, the sequence 5'-A-G-T-3', is complementary to the sequence 3'-T-C-A-5'. Complementarity can be "partial", in which only some of the nucleic acid bases are matched according to the base pairing rules. On the other hand, there may be "complete" or "total" complementarity between the nucleic acid strands when all of the bases are matched according to base pairing rules. The degree of complementarity between nucleic acid strands has significant effects on the efficiency and strength of hybridization between nucleic acid strands as known well in the art. This is of particular importance in detection methods that depend upon binding between nucleic acids, such as those of the invention. The term "substantially complementary" refers to any probe that can hybridize to either or both strands of the target nucleic acid sequence under conditions of low stringency as described below or, preferably, in polymerase reaction buffer (Promega, M195A) heated to 95° C. and then cooled to room temperature. As used herein, when the nucleic acid probe is referred to as partially or totally complementary to the target nucleic acid, that refers to the 3'-terminal region of the probe (i.e. within about 10 nucleotides of the 3'-terminal nucleotide position).

As used herein, the term "hybridization" is used in reference to the pairing of complementary nucleic acid strands. Hybridization and the strength of hybridization (i.e., the strength of the association between nucleic acid strands) is impacted by many factors well known in the art including the degree of complementarity between the nucleic acids, stringency of the conditions involved affected by such conditions as the concentration of salts, the $T_m$ (melting temperature) of the formed hybrid, the presence of other components (e.g., the presence or absence of polyethylene glycol), the molarity of the hybridizing strands and the G:C content of the nucleic acid strands.

As used herein, the term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required when it is desired that nucleic acids which are not completely complementary to one another be hybridized or annealed together. The art knows well that numerous equivalent conditions can be employed to comprise low stringency conditions.

As used herein, the term "$T_m$" is used in reference to the "melting temperature". The melting temperature is the temperature at which 50% of a population of double-stranded nucleic acid molecules becomes dissociated into single strands. Equations for calculating the $T_m$ of nucleic acids are well-known in the art. The $T_m$ of a hybrid nucleic acid is often estimated using a formula adopted from hybridization assays in 1 M salt, and commonly used for calculating $T_m$ for PCR primers: $T_m=[(\text{number of A+T})\times 2° \text{ C. }+(\text{number of G+C})\times 4° \text{ C}]$. C. R. Newton et al. *PCR*, $2^{nd}$ Ed., Springer-Verlag (New York: 1997), p. 24. This formula was found to be inaccurate for primers longer that 20 nucleotides. Id. Other more sophisticated computations for $T_m$ exist in the art which take structural as well as sequence characteristics into account for the calculation of $T_m$. A calculated $T_m$ is merely an estimate; the optimum temperature is commonly determined empirically.

The term "homology", as used herein, refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous".

When used in reference to a double-stranded nucleic acid sequence such as a cDNA or genomic clone, the term "substantially homologous", as used herein, refers to a probe that can hybridize to a strand of the double-stranded nucleic acid sequence under conditions of low stringency.

When used in reference to a single-stranded nucleic acid sequence, the term "substantially homologous", as used herein, refers to a probe that can hybridize to (i.e., is the complement of) the single-stranded nucleic acid template sequence under conditions of low stringency.

The term "interrogation position", as used herein, refers to the location of a given base of interest within a nucleic acid probe. For example, in the analysis of SNPs, the "interrogation position" in the probe is in the position that would be complementary to the single nucleotide of the target that may be altered from wild type. The analytical output from a method of the invention provides information about a nucleic acid residue of the target nucleic acid that is complementary to an interrogation position of the probe. An interrogation position is within about ten bases of the actual 3'-terminal nucleotide of the nucleic acid probe, although not necessarily at the 3'-terminal nucleotide position. The interrogation position of the target nucleic acid sequence is opposite the interrogation position of the probe, when the target and probe nucleic acids are hybridized.

The term "identifier nucleotide", as used herein, refers to a nucleotide whose presence is to be detected in a process of the invention to identify that a depolymerization reaction-has occurred. The particular application of a method of the invention affects which residues are considered an identifier nucleotide.

For a method using ATP detection (e.g. luciferase/luciferin or NADH) wherein, during analysis, all nucleotides released in the depolymerization are "converted" to ATP with an enzyme such as NDPK in the presence of ADP with the released nucleotide providing the phosphate transfer group, all nucleotides released are identifier nucleotides. Similarly, for a method using absorbance detection that does not distinguish between nucleotides, all released nucleotides are identifier nucleotides. For a mass spectrometric detection wherein all the released nucleotides are analyzed, all released nucleotides can be identifier nucleotides; alternatively a particular nucleotide (e.g. a nucleotide analog having a distinctive mass) can be detected. For fluorescence detection, a fluorescently-labeled nucleotide is an identifier nucleotide. The nucleotide can be labeled prior to or after release from the nucleic acid. For radiographic detection, a radioactively-labeled nucleotide is an identifier nucleotide. In some cases, the release of identifier nucleotide is deduced by analyzing the remainder of the probe after a depolymerization step of the invention. Such analysis is generally by a determination of the size or mass of the remaining probe and can be by any of the described analytical methods (e.g. a fluorescent tag on the 5'-terminus of the probe to monitor its molecular weight following capillary electrophoresis).

The term "sample", as used herein, is used in its broadest sense. A sample suspected of containing a nucleic acid can comprise a cell, chromosomes isolated from a cell (e.g., a spread of metaphase chromosomes), genomic DNA, RNA, cDNA and the like.

The term "detection", as used herein, refers to quantitatively or qualitatively identifying a nucleotide or nucleic acid within a sample.

The term "depolymerization", as used herein, refers to the removal of a nucleotide from the 3' end of a nucleic acid.

The term "allele", as used herein, refers to an alternative form of a gene and the term "locus", as used herein, refers to a particular place on a nucleic acid molecule.

BRIEF DESCRIPTION OF THE DRAWING

In the drawings forming a portion of this disclosure, FIG. 1 illustrates the annealing of the 10865 oligonucleotide (SEQ ID NO:1) to 10870 wild type (SEQ ID NO:3) and 10994 mutant (SEQ ID NO:4) oligonucleotides utilized in rolling circle amplification as FIG. 1A and FIG. 1B, respectively. Also shown are the annealing (hybridization) of oligonucleotide 10866 (SEQ ID NO:2) to oligonucleotide 10865, as well as the hybridization of oligonucleotide probe 10869 (SEQ ID NO:5) to oligonucleotide 10870 and of oligonucleotide probe 10989 (SEQ ID NO:6) to oligonucleotide 10994 as representations of the binding of those probes to the respective amplified sequences.

DETAILED DESCRIPTION OF THE INVENTION

Nucleic acid amplification and detection compositions and methods of this invention are useful in determining the presence or absence of predetermined (known) nucleic acid target sequence(s) in a nucleic acid sample. Such compositions and methods utilize an enzyme that can depolymerize the 3'-terminus of an oligonucleotide probe hybridized to the nucleic acid target sequence to release one or more identifier nucleotides whose presence or absence can then be determined as an analytical output that indicates the presence or absence of the target sequence.

In some embodiments, depolymerization reactions of the invention are used to interrogate the identity of a specific base in a nucleic acid. For example, after amplification of a crude nucleic acid sample, the identity of single base point mutations, deletions, or insertions in a nucleic acid can be determined using any of the detection methods of the present invention described in the parent application, U.S. patent application Ser. No. 09/358,972, incorporated herein by reference.

A unifying principle of the nucleic acid amplification and detection methods of the invention is that they involve the detection of a nucleic acid hybrid. The nucleic acid hybrid detection methods of the invention are described in great detail in the parent application cited above.

The various currently known methods for amplifying the nucleic acid target in a sample are discussed first. Such amplification is useful for enhancing the sensitivity of the nucleic acid determination. Then the general methods of the invention for the determination of the presence or absence of a predetermined nucleic acid target sequence are discussed, from probe hybridization to depolymerization of the hybrid to analysis of the depolymerization products.

In a contemplated detection method, a nucleic acid target is "predetermined" in that its sequence must be known to design a probe that hybridizes with that target. A nucleic acid target sequence is predetermined in that a nucleic acid probe is provided to be partially or totally complementary to that nucleic acid target sequence. A nucleic acid target sequence is a portion of nucleic acid sample with which the probe hybridizes if that target sequence is present in the sample.

However, it should be noted that a nucleic acid target sequence, as used with respect to a process of this invention can merely act as a reporter to signal the presence of a different nucleic acid whose presence is desired to be determined, for example in one of the rolling circle replication embodiments discussed below. Furthermore, a process of the invention is useful in determining the identity of a base within a target where only enough of the sequence is known to design a probe that hybridizes to that target with partial complementarity at the 3'-terminal region of the probe.

1. Amplification of the Sample Target or a Detection Target

Broadly, the nucleic acid detection method of the present invention can use any of the amplification techniques known in the art. The most widely used amplification methods at the present time are PCR methods.

Several of the amplification methods are useful in improving the signal from a nucleic acid hybrid detection step, for example by isolating one nucleic acid strand containing a nucleic acid target. An example of this is T7 exonuclease 6 digestion of one amplified strand whereas the other strand of the amplification product is protected by using a primer with phosphorothioate linkages. This is illustrated in Examples 10 and 11 herein using PCR amplification, and is further discussed along with other contemplated signal improvements in the parent application U.S. patent application Ser. No. 09/358,972, filed on Jul. 21, 1999, and incorporated herein by reference.

A. Polymerase Chain Reaction (PCR)

The polymerase chain reaction (PCR) process is well known in the art. U.S. Pat. Nos. 4,683,195, 4,683,202, and 4,800,159, the disclosures of which are incorporated herein by reference; Saiki, et al., *Science*, 230:1350 (1985); Patterson et al., *Science*, 260:976 (1993) describe processes to amplify a nucleic acid sample target using PCR amplification primers that hybridize with the sample target. Example 6 illustrates a multiplex embodiment of the invention that utilizes PCR techniques.

To briefly summarize PCR, nucleic acid primers, complementary to opposite strands of a nucleic acid amplification target sequence, are permitted to anneal to the denatured sample. A DNA polymerase (typically heat stable) extends the DNA duplex from the hybridized primer. As the PCR amplification primers are extended, more sample target is made so that more primers can be used to repeat the process, thus amplifying the sample target sequence. Typically, the reaction conditions are cycled between those conducive to hybridization and nucleic acid polymerization, and those that result in the denaturation of duplex molecules. The process is repeated to amplify the nucleic acid target. If the nucleic acid primers do not hybridize to the sample, then there is no corresponding amplified PCR product.

The PCR reaction is capable of exponentially amplifying the desired nucleic acid sequences, with a near doubling of the number of molecules having the desired sequence in each cycle. Thus, by permitting cycles of hybridization, polymerization, and denaturation, an exponential increase in the concentration of the desired nucleic acid molecule can be achieved. Reviews of the technique include K. Mullis, *Cold Spring Harbor Symp. Quant. Biol.*, 51:263–273 (1986); C. R. Newton & A. Graham, *Introduction to Biotechniques: PCR*, $2^{nd}$ Ed., Springer-Verlag (New York: 1997).

In a contemplated process of the invention, PCR primers are selected that will amplify a region of nucleic acid from a nucleic acid sample source that contains the nucleic acid target sequence. In some contemplated processes of the invention, one of the PCR amplification primers comprises phosphorothioate or an analogous linkage that will protect one strand of a nucleic acid amplification product from exonuclease digestion. Treatment of the amplification product with an exonuclease, such as T7 gene 6 exonuclease (also called T7 exonuclease 6 herein), will then leave intact one of the amplification product strands containing the nucleic acid target for a detection process of the invention. The use of PCR amplification with strand removal is illustrated in the examples below.

B. Ligase Chain Reaction (LCR) and Repair Chain Reaction (RCR)

Ligase Chain Reaction (LCR) and Repair Chain Reaction (RCR) are very similar techniques, where in ligase chain reaction two primers are linked, in repair chain reaction a gap is filled in between two primers with a polymerase and they are linked. The two similar amplification methods are contemplated as part of a nucleic acid amplification and detection processes of the invention. Example 3 illustrates an embodiment of the invention utilizing ligase chain reaction.

Ligase Chain Reaction is an amplification process well known in the art. U.S. Pat. No. 5,516,663, European Patent No. EP-A-320 308, European Patent No. EP-A-439 182; Barany, *Proc. Natl. Acad. Sci., USA*, 88:189 (1991). In LCR, two adjacent amplification primers, as well as two others that are complementary to them, are present in excess in the amplification reaction that also contains DNA ligase. The amplification primers hybridize to the complementary sequence in the sample target, such that the adjacent primers are substrates for ligase only when hybridized to the sample target. Ligase links the two adjacently hybridized amplification probes. In a succession of temperature cycles, preferably with use of a thermostable ligase, the linked probes separate from the target and can, in turn, serve as target sequence for other amplification probes (Barany, *Proc. Natl. Acad. Sci., USA*, 88:189–193 1991).

In another amplification method discussed in International Patent Application publication number WO 90/01069, the nucleic acid of interest is amplified from the crude nucleic acid sample using a repair chain reaction (RCR) method prior to detection of the target. In a RCR method of amplification, two oligonucleotide amplification primers that are complementary to the amplification target and two other primers (complementary to the extension product) are provided in excess in the presence of a thermostable DNA ligase and a thermostable DNA polymerase. When a nucleic acid sample target sequence is present, the amplification primers hybridize to the nucleic acid sample at either side of the amplification target leaving a gap between the otherwise adjacently hybridized primers. The gap is filled in with DNA polymerase and then ligated with DNA ligase to form a complete complementary copy of the amplification target with the primer on either end. By a succession of temperature cycles, as in PCR and LCR, the extended primers linked to the amplification primers can in turn serve as target for new primers.

In some ligase chain reaction embodiments, the ligase chain reaction primers are two short linear oligonucleotide primers that are linked to form a longer linear oligonucleotide. Preferably in these embodiments of the present invention, a nucleic acid probe will hybridize to the region where the primers are linked so that the analytical output in a process of the invention will remain at about background levels if the ligase chain reaction primers are not linked, which happens when a nucleic acid strand that is complementary to the nucleic acid target is not present.

In some preferred embodiments, several methods of the invention contemplate the determination of the presence or absence of a predetermined nucleic acid target in a nucleic acid sample using an open circle primer. The predetermined nucleic acid sample target has a 5' region and a 3' region and will be considered a "sense" strand for reference purposes.

An open circle first probe has three regions. The open circle probe has a 5'-terminal region (the first region of the open circle probe) that hybridizes to a 3' region of a nucleic acid sample target and a 3'-terminal region (the third region of the open circle probe) that hybridizes to a 5' region of a nucleic acid sample target that may be RNA or DNA. The second region is the between the 3'-and 5'-terminal regions. The circular detection probe is DNA that is antisense relative to the nucleic acid sample target.

The proper hybridization of the 5'- and 3'-terminal regions of the open circle probe to the predetermined nucleic acid sample target brings the 5'- and 3'-terminal ends of the open circle probe into proximity of each other. The two ends of the open circle probe can be linked together using ligase, or if there are several bases between the two ends a process of the invention contemplates that the intervening bases can be filled in using DNA polymerase or an oligo and then linked using ligase. The linkage of the two ends of the open circle probe results in a closed circular probe that is hybridized to the predetermined nucleic acid sample target. If the predetermined nucleic acid sample target is absent, then the open circle probe is unaffected by ligase.

An amplification primer hybridizes to a portion of the second region of the closed circular probe. In a contemplated amplification step, a DNA chain is extended from the amplification primer using a DNA polymerase that has displacement activity. An extension product from the amplification primer is complementary to the second region of the closed circular probe.

If the open circle probe has not been ligated, amplification will only proceed through the 5'-terminal region (the first region) of the open circle probe. DNA complementary to the portion of the open circle primer from 3'-terminal region (the third region) through the portions of the second region up to the amplification primer hybridization site is not made unless open circle primer has been ligated to form a closed circular primer.

With a closed circular probe, DNA complementary to the entire closed circular probe is replicated, including a detection target sequence that is complementary to the detection probe (sometimes referred to as an interrogation probe). Hybridization of the detection probe to the replicated detection target sequence is ascertained in a process of the invention by depolymerization of the hybridized nucleic acid to release identifier nucleotides and analyzing for the presence of those identifier nucleotides.

Such processes of the invention using circular probes contemplate three target sequences: a predetermined nucleic acid sample target, an amplification target and a detection target. A sequence complementary to the detection target is typically designed into the open circle probe. A process contemplates that the detection target complement is not in the first region of the open circle probe (the 5'-terminal region), but is either in the second or third region that will only be replicated if the open circle probe has been ligated to a closed circle primer.

C. Amplification Refractory Mutation (ARMS)

Another preferred amplification technique, a common PCR-based method for determining the presence or absence of a specific known nucleic acid sequence, such as a mutation (e.g. a genetic polymorphism), is called an amplification refractory mutation system (ARMS). This amplification method is also known as allele-specific PCR (ASPCR), PCR amplification of specific alleles (PASA) or allele-specific amplification (ASA). Example 4 illustrates an embodiment of the invention utilizing ARMS.

In a typical ARMS assay of the art, two PCR reactions using different PCR primers are conducted on the same nucleic acid sample. Each of the two PCR primers is designed to have a residue at the 3'-terminus of the primer that is complementary to one of the two allelic variants and not to the other. The PCR reaction does not extend from a primer having a 3'-terminal mismatched base, unless the polymerase used has a 3' to 5' proofreading activity that removes the mismatched base and inserts the correct base. Proofreading repairs the PCR primer and destroys the extension discrimination between the two alleles. Therefore, a polymerase lacking a 3' to 5' proofreading activity, such as Taq DNA polymerase, is used in such an ARMS assay. The extension products are typically ascertained after agarose gel electrophoresis with ethidium bromide staining. In a contemplated process of the present invention, an appropriate nucleic acid probe can be used to determine the presence or absence of a nucleic acid target sequence in the extension products.

ARMS has been applied to SNP determination. Two amplification reactions are used to determine if a SNP is present in a DNA sample. Newton et al. *Nucl. Acids Res.,* 17:2503 (1989); Wu et al., *Proc. Natl. Acad. Sci., USA,* 86:2757 (1989). Both amplification reactions contain a common primer for the target of interest. The first reaction contains a second primer specific for the wild type product which will give rise to a PCR product if the wild type gene is present in the sample. The second PCR reaction contains a primer that has a single nucleotide change at or near the 3' end that represents the base change that is present in the mutated form of the DNA. The second primer, in conjunction with the common primer, will only function in PCR if genomic DNA that contains the mutated form of genomic DNA is present. As carried out in the art, this technique requires duplicate amplification reactions to be performed and analyzed by gel electrophoresis to ascertain if a mutated form of a gene is present. As contemplated with the present invention, duplicate amplification reaction products can be hybridized with a probe to the wild type or mutated form. Alternatively, differently labeled or otherwise distinguishable probes can be used in on a single amplification reaction product to detect presence or absence of an SNP.

In the art, it is known that the discrimination between specificity of PCR extension from the allele-specific ARMS primers is enhanced by the introduction of deliberate mismatches near the 3'-terminal nucleotide, although possibly also decreasing overall PCR extension product yield. Other factors known to affect the stability of the hybridization of PCR primers in an ARMS assay include the position of additional mismatches in the primer, the GC content of the 5 or 6 nucleotides preceding the 3' nucleotide, and the discriminatory 3'-terminal nucleotide, depending on the difference between the alleles and the type of mismatch. The destabilization is greater when the second mismatch is nearer to the 3'-terminal nucleotide. The destabilizing effect of additional mismatches on ARMS has been ranked qualitatively (CC>CT>GG=AA=AC>GT).

D. Extension

A process of the invention can be used to ascertain matched or mismatched bases at the discriminatory 3'-terminal nucleotides in place of conducting PCR extension, as demonstrated in Example 4. Similar factors are thought to affect the stability of hybrids in a process of the invention as has been noted with ARMS, so preferably, such considerations are taken into effect when designing probes for use in process of the invention.

E. Amplification with Incorporation of Restriction Endonuclease Site

A contemplated method can be used to determine the presence or absence in a nucleic acid sample of a restriction endonuclease recognition sequence that cleaves double-stranded DNA leaving a 5' overhang or a blunt end. In this embodiment of the invention, the nucleic acid hybrid is thus "preformed" and the hybrid is depolymerized according to the invention. The cleavage product is a nucleic acid target that is a substrate for an enzyme whose activity is to release one or more nucleotides from the 3'-terminus in a process of the invention. Example 5 illustrates an embodiment of the invention utilizing restriction endonuclease digestion.

The use of restriction enzymes that leave 5' overhangs or a blunt end after cleavage are contemplated for use in a claimed process. Such restriction enzymes are well known in the art. The enzymes are commercially available from several companies, including Promega Corp. in Madison, Wis. A list of some such enzymes can be found in Sambrook et al., *Molecular Cloning: A Laboratory Manual*, $2^{nd}$ Ed., Cold Spring Harbor Laboratory Press (Plainview, N.Y., 1989).

One contemplated process uses the detection of a restriction endonuclease site to indirectly detect the presence or absence of a certain nucleic acid within a sequence, such as an SNP. In such a process, the sequence adjacent downstream of an SNP in a nucleic acid target is used to design a PCR primer for a PCR amplification that is complementary to the downstream sequence SNP in a first region of the PCR primer. Preferably, the 3'-terminal portion of the PCR primer is used to determine the presence or absence of the SNP.

Thus, the 3'-terminal residue of the PCR primer either matches or mismatches with the SNP. Preferably, a destabilizing mismatch is incorporated into this PCR primer, as described above, to enhance the specificity of PCR extension from the PCR primer when the 3'-terminal residue matches the SNP.

A second region of the PCR primer introduces a restriction endonuclease recognition site into the PCR products. The restriction endonuclease recognition sequence is selected to provide a substrate for a depolymerization reaction of the invention. The PCR reaction is conducted and the product purified. The PCR product is treated with the restriction endonuclease to cleave at its recognition site leaving a restriction endonuclease cleavage product containing an identifier nucleotide.

A depolymerizing enzyme of the invention is admixed with the PCR product either before or after restriction endonuclease cleavage. The admixture is analyzed for the release of identifier nucleotide after maintaining the admixture under depolymerizing conditions for a time period sufficient for depolymerization. As noted herein, the identifier nucleotide need not be a nucleotide analog, but it is possible if a nucleotide analog, including a fluorescently labeled nucleotide, were present in the original PCR primer that became the restriction endonuclease recognition sequence. As discussed elsewhere herein, the release of identifier nucleotide is ascertained by analyzing the released nucleotide or the remaining probe.

F. Rolling Circle Replication

Rolling circle replication is described in U.S. Pat. No. 5,854,033, the disclosures of which are incorporated herein by reference. Rolling circle replication reporter systems are useful in detecting the presence of nucleic acid molecules of interest, and in amplifying target sequences—either of the nucleic acid sequence of interest or of a reporter signifying its presence. In a contemplated embodiment of the present invention, such amplification and reporter systems are used in conjunction with a hybridization analysis process of the present invention. Examples 1, 2 and 7 illustrate rolling circle embodiments of the present invention. Example 7 is an example of a dual probe rolling circle embodiment of the invention.

Several methods of the invention contemplate the determination of the presence or absence of a predetermined nucleic acid target in a nucleic acid sample using an open circle primer. The predetermined nucleic acid sample target has a 5' region and a 3' region and will be considered a "sense" strand for reference purposes.

An open circle first probe has three regions. The open circle probe has a 5'-terminal region (the first region of the open circle probe) that hybridizes to a 3' region of a nucleic acid sample target and a 3'-terminal region (the third region of the open circle probe) that hybridizes to a 5' region of a nucleic acid sample target that may be RNA or DNA. The second region is the between the 3'-and 5'-terminal regions. The circular detection probe is DNA that is antisense relative to the nucleic acid sample target.

The proper hybridization of the 5'- and 3'-terminal regions of the open circle probe to the predetermined nucleic acid sample target brings the 5'- and 3'-terminal ends of the open circle probe into proximity of each other. The two ends of the open circle probe can be linked together using ligase, or if there are several bases between the two ends a process of the invention contemplates that the intervening bases can be filled in using DNA polymerase or an oligo and then linked using ligase. The linkage of the two ends of the open circle probe results in a closed circular probe that is hybridized to the predetermined nucleic acid sample target. If the predetermined nucleic acid sample target is absent, then the open circle probe is unaffected by ligase.

An amplification primer hybridizes to a portion of the second region of the closed circular probe. In a contemplated amplification step, a DNA chain is extended from the amplification primer using a DNA polymerase that has displacement activity. An extension product from the amplification primer is complementary to the second region of the closed circular probe.

If the open circle probe has not been ligated, amplification will only proceed through the 5'-terminal region (the first region) of the open circle probe. DNA complementary to the portion of the open circle primer from 3'-terminal region (the third region) through the portions of the second region up to the amplification primer hybridization site is not made unless open circle primer has been ligated to form a closed circular primer.

With a closed circular probe, DNA complementary to the entire closed circular probe is replicated, including a detection target sequence that is complementary to the detection probe (sometimes referred to as an interrogation probe). Hybridization of the detection probe to the replicated detection target sequence is ascertained in a process of the invention by depolymerization of the hybridized nucleic acid to release identifier nucleotides and analyzing for the presence of those identifier nucleotides.

Such processes of the invention using circular probes contemplate three target sequences: a predetermined nucleic acid sample target, an amplification target and a detection target. A sequence complementary to the detection target is typically designed into the open circle probe. A process contemplates that the detection target complement is not in the first region of the open circle probe (the 5'-terminal region), but is either in the second or third region that will only be replicated if the open circle probe has been ligated to a closed circle primer.

In an alternative contemplated amplification step, an RNA transcription origin is located in the circular probe at a position upstream (in the 5' direction) of the closed circle probe relative to a region that is complementary to a detection target. Transcription from this origin occurs in the 5' to 3' direction of the transcript, which makes RNA complementary to the first region of the open circular transcript and then stops unless the circle has been ligated. If the circle were ligated to a closed circular probe, then the RNA transcript will run around the circle and transcribe a region complementary to the detection target. No stop codons should be in the region of the closed circular primer between the region complementary to the detection target and the transcription origin.

G. Other Amplification Methods

In another amplification method, the nucleic acid of interest is amplified from the crude nucleic acid sample using an amplification of transcripts (TAS) method prior to detection of the target. In a TAS amplification method, such as that described in international patent application publication number WO 88/10315, an amplification cycle comprises three stages.

In the first stage, a cDNA is synthesized from RNA in the presence of reverse transcriptase and a complementary primer also containing an RNA polymerase promoter, such as a phage RNA promoter. Following thermal denaturation of the RNA/cDNA heteroduplex, the single-stranded cDNA is replicated by reverse transcriptase in the presence of an antisense amplification primer. The DNA homoduplex thus obtained during this second stage contains a double-stranded promoter to which a phage DNA-dependent RNA polymerase can bind. The third stage then consists of transcribing RNA molecules (from 30 to 1000 per template) which can serve as template for the synthesis of additional cDNA to continue the amplification cycle. Davis et al., *J. Infect. Dis.*, 162:13–20 (1990).

In yet another method, the nucleic acid of interest is amplified from the crude nucleic acid sample using a method similar to TAS, such as self-sustained sequence replication (3SR), nucleic acid sequence-based amplification (NASBA), and single primer sequence replication (SPSR), as an amplification method prior to detection of the target using depolymerization according to the invention. 3SR is described in international patent application publication number WO 90/06995 and Guatelli et al, *Proc. Natl. Acad. Sci., USA,* 87:1874–1878 (1990). NASBA is described in European Patent No. 0,373,960. SPSR is described in U.S. Pat. No. 5,194,370, the disclosures of which are herein incorporated by reference. These three methods use RNA- and DNA-dependent DNA polymerases (reverse transcriptase), ribonuclease H (RNase H; *Escherichia coli* enzyme and/or enzymatic activity associated with reverse transcriptase) and DNA-dependent RNA polymerase (T7 bacteriophage RNA polymerase).

Briefly, at a fixed temperature (37° C.–47° C.), a continuous process of reverse transcription and transcription reactions are conducted by methods well-known in the art in order to replicate an RNA target via cDNA. The RNA polymerase binding site (e.g. T7 phage RNA polymerase site) is introduced by the primer used for the reverse transcription stage of the reaction. The isothermal denaturation of the RNA/cDNA heteroduplex is effected by specific hydrolysis of the RNA using RNase H activity. The free cDNA is replicated from a second oligonucleotide by reverse transcriptase. The resulting DNA/DNA homoduplex is transcribed into RNA by, for example, T7 RNA polymerase. The product RNA can serve as a template to repeat the amplification cycle.

In a further method, the nucleic acid of interest is amplified from the crude nucleic acid sample using a ligation activated transcription (LAT) method prior to detection of the target. LAT is described in U.S. Pat. No. 5,194,370, whose disclosures are incorporated herein by reference.

A person of ordinary skill in the art at the time of practicing the invention will recognize that any amplification method known in the art at the time of practicing the invention can be usefully combined with a nucleic acid hybrid detection method of the invention. There are other amplification methods now known in the art that are not discussed herein in detail, though they are contemplated and equally useful in a process of the invention; for example Strand Displacement Amplification (SDA) is described in Walker et al., *Nucl. Acids Res.,* 20:1691 (1992), and Qβ replicase amplification (QβRA) is described in Wu et al., *Proc. Natl. Acad. Sci., USA,* 89:11769 (1992); Lomeli et al., *Clin. Chem.,* 35:1826 (1989).

2. Hybridization

In one embodiment, the hybrid is formed by admixing a sample to be assayed for the presence of a nucleic acid hybrid with one or more nucleic acid probes. The admixing is typically carried out under low stringency hybridizing conditions to form a hybridization composition. In such a hybridization composition, the 3'-terminal region of the nucleic acid probes (i) hybridize with partial or total complementarity to a nucleic acid target sequence that may be present in the sample; and (ii) include an identifier nucleotide in the 3'-terminal region.

A nucleic acid probe comprises single-stranded nucleic acid (e.g., DNA or RNA). A probe can be of varying lengths, preferably from about 10 to 1000 based, most preferably about 10 to 100 bases, with about 10 to 30 bases particularly preferred. In preferred embodiments, a probe is complementary to the target at all bases between an interrogation position and 3' end of the nucleic acid probe.

In one embodiment, each nucleic acid probe synthesized is substantially complementary to a target nucleic acid containing or suspected of containing a point mutation. It will be recognized that various hybridization conditions can be used, so as to vary the stringency at which hybridization occurs. Thus, depending upon the system utilized, the complementarity of the probe can be varied. Depending on the length of the probe, the GC content, and the stringency of the hybridization conditions, the probe can have as many as 10 base mismatches with the target nucleic acid, and preferably less than 5 mismatches. Most preferably, the probe has only one base mismatch with the target nucleic acid or is completely complementary to the target nucleic acid.

In some preferred embodiments, a probe is designed to have a predetermined nucleotide at an interrogation position. When a complementary probe base pairs or hybridizes to a target nucleic acid, the base at an interrogation position aligns with the base in the nucleic acid target whose identity is to be determined under conditions such that base pairing can occur. It is contemplated that an interrogation position can be varied within the probe. For example, in some preferred embodiments, an interrogation position is preferably within 10 bases of the 3' end of the nucleic acid probe. In still other preferred embodiments, an interrogation position is within 6 bases of the 3' end of the nucleic acid probe. In particularly preferred embodiments, an interrogation position is at the next to last or last base at the 31 end of the nucleic acid probe.

Preferably, a nucleic acid probe is designed to not hybridize with itself to form a hairpin structure in such a way as to interfere with hybridization of the 3'-terminal region of the probe to the target nucleic acid. Parameters guiding primer design for PCR and other nucleic acid hybridization techniques to are well known in the art and are applicable to probe design for the present invention.

The ability to interrogate the identity of a specific base in a nucleic acid also permits discrimination between nucleic acids from different species, or even from different alleles. The ability to detect and discriminate between nucleic acids of related or unrelated species also permits the identification of species contained within a given nucleic acid-containing sample. For example, the method can be used to determine which species of several related bacteria or virus are contained within a sample (e.g., clinical samples, environmental samples, food samples, or samples from non-human animals).

An interrogation position can be varied within the probe. For example, an interrogation position is preferably within 10 bases of the 3' end of the nucleic acid probe. More preferably, an interrogation position is within 6 bases of the 3' end of the nucleic acid probe. Most preferably, an interrogation position is at the next to last or last base of the 3' end of the nucleic acid probe.

The nucleic acid probes are designed so that the base at an interrogation position is complementary to the nucleotide at the predetermined position of one species or allele, but not another due to the mismatch. Likewise, a second probe can be synthesized that is complementary at an interrogation position to the nucleotide at the predetermined position of a second species or allele.

A contemplated procedure is employed to identify the presence or absence of multiple species within a given sample. In these embodiments, all that is required is the identification of substantially identical sequences between species that contain base mismatches or the identification of a nucleic acid sequence unique to each species to be identified.

A method contemplated by the present invention has wide applicability in assaying nucleic acids. In some aspects, an endogenous nucleic acid is assayed to determine whether a particular native or mutant sequence is present or absent. This type of analysis is sometimes referred to as genotyping because the genetic makeup of the subject from which the nucleic acid sample is obtained is determined. Speciation, the identity of an organism, such as the identification of a human, dog, chicken, bovine or the like can be determined by use of species-specific nucleic acid probes such as probes to selected regions of the gene encoding cytochrome B.

Using a contemplated method, one can illustratively determine whether a human patient, for example, has the Leiden V mutation, a mutant β-globin gene, the cystic fibrosis-related gene in the region of the delta 508 allele, a mutation in a prothrombin gene, congenital adrenal hyperplasia, a translocation that takes place in the region of the bcr gene along with involvement of a segment of the abl gene, the number of repeated sequences in a gene such as are present in THO 1 alleles or the TPOX alleles, as well as the loss of heterozygosity of the locus of certain alleles as is found in certain cancers and also allelic trisomy. Genomic typing can also be used to assay plant genomes such as that of rice, soy or maize to determine if they contain non-native sequence. The presence or absence in a sample of the genomes of microbes such as *Campylobacter jejuni*, Listeria, and *E. coli* 0H157 can be determined, and viral genomes such as that of cytomegalovirus (CMV) or human immunodeficiency virus (HIV) can be analyzed to determine whether a drug-resistant strain is present in a sample.

A contemplated method can also be utilized to assay for the presence or absence of nucleic acid that is exogenous to the source of the sample. For example, a contemplated method can be used to assay for the presence of viruses such as hepatitis C virus (HCV), cytomegalovirus (CMV), human immunodeficiency virus (HIV), as well as to determine the viral load in an organism with a disease, such as a human or a plant. A contemplated method can also be used to identify the presence of an exogenous nucleic acid sequence in a plant such as maize, soy or rice. A contemplated method can also be used to assay for the presence of microorganisms such as *Listeria monocytogenes*, Campylobacter spp., Salmonella spp., Shigella spp. or *Escherichia coli* (including *E. coli* E0157) in foodstuffs such as meats, dairy products, and fruit juices.

The determination of an appropriate nucleic acid target sequence useful for designing nucleic acid probes for use in a method of the invention is within the skill of the art. Databases of genetic sequences, such as Genbank, can be used to ascertain the uniqueness of the selected nucleic acid target. Commercially available software for designing PCR primers can be used to assist in the design of probes for use in the invention.

The hybridization composition is maintained under hybridizing conditions (discussed hereinafter) for a time period sufficient to form a treated sample that may contain one or more predetermined nucleic acid target sequences hybridized with their respective nucleic acid probes.

In the event that the sample to be assayed does not contain a target sequence to which the probe hybridizes, no hybridization takes place upon forming a treated sample. However, in an embodiment wherein a treated sample is formed, the sample is still admixed with the probe(s) and maintained under conditions that would permit hybrid formation if a nucleic acid target is present. When a method of the present invention is used to determine whether a particular target sequence is present or absent in a sample to be assayed, the resulting treated sample may not contain a substrate for the depolymerizing enzymes of the present invention. As a result, a 3' terminal region identifier nucleotide is not released and the analytical output is at or near background levels.

With any method of the present invention, hybridization conditions can be empirically ascertained for a control sample for various time periods, pH values, temperatures, nucleic acid probe/target combinations and the like. Exemplary maintenance times and conditions are provided in the specific examples hereinafter and typically reflect low stringency hybridization conditions. In practice, once a suitable set of hybridization conditions and maintenance time periods are known for a given set of probes, an assay using those conditions provides the correct result if the nucleic acid target sequence is present. Typical maintenance times are about 5 to about 60 minutes.

The conditions and considerations with respect to hybridization of PCR primers to template nucleic acid in PCR are applicable to the hybridization of nucleic acid probes to target sequences in a process of the invention. Such hybridization conditions are well known in the art, and are a matter of routine experimentation depending on factors including the sequence of the nucleic acid probe and the target nucleic acid [sequence identity (homology), length and G+C content] molar amounts of nucleic acid present, buffer, salt content and duplex $T_m$ among other variables.

Processes of the invention are sensitive and hybridization conditions of low stringency (e.g. temperature of 0–4° C.) are sufficient; but moderate stringency conditions (i.e. temperatures of 40–60° C.) also permit hybridization and provide acceptable results. This is true for all processes of the invention.

Processes of the invention can also be concerned with the degree of hybridization of the target to the 3'-terminal region of the probe. Examples in the parent application, U.S. patent application Ser. No. 09/358,972, filed Jul. 21, 1999, show that the distinction between a matched and mismatched base becomes less notable as a single mismatch is at a position further upstream from the 3'-terminal region position. There is very little discrimination between a match and mismatch when a single mismatch is ten to twelve residues from the 3'-terminal nucleotide position, whereas great discrimination is observed when a single mismatch is at the 3'-terminus. Therefore, when the degree of complementarity (partial or total complementarity) of a nucleic acid probe hybridized to a target nucleic acid sequence is referred to herein in regard to an identifier nucleotide, this is to be understood to be referring to within the 3'-terminal region, up to about ten residues of the 3'-terminal position.

In particular embodiments of the invention, it is desirable to include a destabilizing mismatch in or near the 3'-terminal region of the probe. In an example of such an embodiment, the goal is to determine whether a nucleotide at an interrogation position is a match or a mismatch with the target. Better discrimination between match and mismatch at the interrogation position is observed when an intentional mismatch is introduced about 2 to about 10 nucleotides from the interrogation position or preferably about 2 to about 6 nucleotides from the interrogation position.

The distinction of the analytical output between matched and mismatched nucleotides when there is more than a single base that is mismatched within the 3'-terminal region can be evident even if mismatches are beyond position 10 from the terminus, for example at position 11 and 12 upstream of the 3'-terminal nucleotide. Thus, the phrases "about 10" and "3'-terminal region" are used above. The 3'-terminal region therefore comprises the approximately 10 residues from the 3'-terminal nucleotide (or 3' terminus) position of a nucleic acid.

In one embodiment of the invention, a nucleic acid hybrid is formed, and the depolymerization substrate is already present without going through the steps of admixing probe (s) and maintaining under hybridizing conditions. Thus, the "treated sample" is preformed in one embodiment.

3. Depolymerization

The treated sample is admixed with a depolymerizing amount of an enzyme whose activity is to release one or more identifier nucleotides from the 3'-terminus of the probe that is hybridized to the nucleic acid target to form a depolymerization reaction mixture. The choice of enzyme used in the process determines if a match or mismatch at the 3'-terminal nucleotide results in release of that 3'-terminal nucleotide. Further information regarding specific enzymes and depolymerization reaction conditions is discussed in detail hereinafter, and also in the parent cases cited above.

The depolymerization reaction mixture is maintained under depolymerizing conditions for a time period sufficient to permit the enzyme to depolymerize hybridized nucleic acid and release identifier nucleotide therefrom to form a treated reaction mixture.

The presence or absence of released identifier nucleotide is then determined to obtain an analytical output. The analytical output indicates the presence or absence of a nucleic acid target sequence in the sample.

In one contemplated embodiment of the invention, the enzyme whose activity is to depolymerize hybridized nucleic acid to release nucleotides from the probe 3'-terminal end is a template-dependent polymerase that releases nucleotides from a matched 3' terminus. In such an embodiment, the reverse of a polymerase reaction (pryophosphorolysis) is used to depolymerize a nucleic acid probe, and the identifier nucleotide is released most efficiently when the 3'-terminal nucleotide of the nucleic acid probe hybridizes with total complementarity to its nucleic acid target sequence. Thus, in an embodiment using the reverse of a polymerase reaction to depolymerize nucleic acid hybrid, a signal confirms the presence of a nucleic acid target sequence that has the sequence sufficiently complementary to the nucleic acid probe to be detected by the process of the invention.

Various template-dependent polymerases useful in a process or kit of the invention are known in the art, including thermostable polymerases. Preferred template-dependent polymerases are Taq polymerase, Tne polymerase, Tne triple mutant polymerase, Tth polymerase, Tvu polymerase, Ath polymerase, T4 DNA polymerase, Klenow fragment, Klenow exo minus, *E. coli* DNA polymerase I, AMV reverse transcriptase, MMLV reverse transcriptase, or poly(A) polymerase. Particularly preferred template-dependent polymerases are Tne polymerase, Tne triple mutant polymerase, Klenow exo minus, MMLV reverse transcriptase, with Tne triple mutant polymerase being most particularly preferred. For RNA substrates, AMV reverse transcriptase, MMLV reverse transcriptase, or poly(A) polymerase are particularly preferred. The pyrophosphorolysis reaction and enzymes are discussed in more detail in the parent application cited above and is incorporated herein by reference.

As is illustrated in the Examples that follow, it can be beneficial to carry out a contemplated method at elevated temperatures, e.g., about 5° C. to about 90° C. The Tne triple mutant DNA polymerase is described in detail in WO 96/41014, whose disclosures are incorporated by reference, and its 610 residue amino acid sequence is provided as SEQ ID NO:35 of that document. That enzyme is referred to in WO 96/41014 as Tne M284 (D323A,D389A).

Briefly, that enzyme is a triple mutant of the polymerase encoded by the thermophilic eubacterium *Thermotoga neapolitana* (ATCC 49049). The amino-terminal 283 residues of the native sequence are deleted and the aspartic acid residues at positions 323 and 389 of the native sequence are replaced by alanine residues in this recombinant enzyme. This recombinant enzyme is thus a deletion and replacement mutant of the native enzyme.

Deletion of the amino-terminal sequence removes the 5' exonuclease activity of the native enzyme, whereas replacement of the two aspartic acid residues removes a magnesium binding site whose presence facilitates exonuclease activity, and this triple mutant also exhibited no 3' exonuclease activity relative to the recombinant native enzyme. This triple mutant enzyme exhibited a half-life at 97.5° C. of 66 minutes as compared to the full length recombinant enzyme that exhibited a half-life of only 5 minutes at that temperature.

In a preferred embodiment in the case of the reverse of polymerase activity (pyrophosphorolysis), a preferred substrate is a DNA probe hybridized to a nucleic acid target sequence with total complementarity at its 3'-terminus, most preferably including an identifier residue at the 3'-terminal region.

In an embodiment of the invention where the enzyme's activity is a 3' to 5' exonuclease activity, the hybridized nucleic acid probe is depolymerized from its 3'-terminal nucleotide. In an embodiment that uses a 3' to 5' exonuclease activity of a polymerase to depolymerize a nucleic acid probe, the 3'-terminal residue of the nucleic acid probe is released when it is mismatched and therefore there is only partial complementarity of the $3^1$-terminus of the nucleic acid probe to its nucleic acid target sequence. In this embodiment, to minimize background, the hybrid is typically purified from unannealed nucleic acid prior to the enzyme reaction, which releases identifier nucleotides. A signal confirms the presence of a nucleic acid target sequence that is not totally complementary to the nucleic acid probe.

A depolymerization reaction can be catalyzed by bacteriophage T4 polymerase in the absence of NTPs depolymerizes a mismatched hybrid. In preferred embodiments, the released nucleotides, XMPs, are produced by nuclease digestion by the polymerase.

Nuclease digestion can be accomplished by a variety of nucleases that release a nucleotide with a 5' phosphate, including nuclease S1 (converts nicked to two blunt ends; degrades ss DNA or RNA, hybrids are resistant but can be digested completely if swamped with enzyme; used to remove ss tails to blunt ends), nuclease BAL 31 (digests blunt ends down to 5' overhang duplexes to shorter blunt ends—digests both strands one more slowly than the other; also active at nicks; BAL 31 also shortens ssDNA using exonuclease activity, so hybrid should be separated from un-annealed NA for this; also endonuclease cleaves non-B-DNA conformations of dsDNA to ds linear DNA, or further to truncated ds linear DNAs), mung bean nuclease (ss DNA to mono or oligonucleotides; used to convert protruding termini to blunt ends; will attack a nick after it has been enlarged to a gap of several nucleotides), exonuclease III (digests 3' end of blunt or 5' overhangs down to 5' overhangs; won't cleave thioesters) and ribonuclease H. Nuclease digestion conditions and buffers are known in the art. Nucleases and buffers for their use are available from commercial sources.

Various polymerases with 3' to 5' exonuclease activity useful in this embodiment of the invention that uses a 31 to 5' exonuclease activity of a polymerase, to depolymerize a nucleic acid probe are known in the art, also including thermostable polymerases. Such polymerases include *E. coli* DNA polymerase I, Klenow or T4 DNA polymerase. Preferred polymerases with 3' to 5' exonuclease activity useful in this embodiment of the invention are Klenow or T4 DNA polymerase. The depolymerization reaction that uses a 3' to 5' exonuclease activity of a polymerase and enzymes are discussed in more detail in the parent application cited above and is incorporated herein by reference.

In a preferred embodiment in the case of a 3' to 5' exonuclease activity of a polymerase, the preferred substrate is a nucleic acid probe hybridized to a nucleic acid target sequence with partial complementarity at its 3'-terminal region, most preferably with a mismatch at its 3'-terminal residue that is an identifier nucleotide.

In an embodiment that uses a 3' to 5' exonuclease activity of Exonuclease III to depolymerize a nucleic acid probe, an identifier nucleotide is released when the 3'-terminal residue of the nucleic acid probe is matched to the target nucleic acid. A signal confirms the presence of a nucleic acid target that is complementary at the released identifier nucleotide. Preferred enzymes for this embodiment are Exonuclease III, S1 nuclease, nuclease BAL 31, mung bean nuclease, and ribonuclease H, most preferably, Exonuclease III. The depolymerization reaction that uses a 3' to 5' exonuclease activity and the enzymes are discussed in more detail in the parent application cited above and is incorporated herein by reference.

Preferred reaction mixtures for depolymerization, including suitable buffers for each enzyme, are described in greater detail in the parent application and the Examples. Typically, under these conditions, sufficient NTP or dNTP is released to accurately detect or assay extremely low amounts of nucleic acid target (e.g., about 5–1000 picograms).

In some preferred embodiments, oligonucleotide probes are typically utilized at about 100 ng to about 1 $\mu$g per 20 $\mu$L depolymerization reaction. That amount provides a probe to target weight ratio of about 200:1 to about 1,000:1.

In a preferred embodiment of the present invention, nucleic acid polymerase and pyrophosphate ($PP_i$) or an analogue thereof, are added to a hybridized sample containing from less than about 100 $\mu$g of target nucleic acid, to less than about 10 pg of nucleic acid. Typical target nucleic acids are present at about 1 to about 5 ng in the sample to be assayed, with a target nucleic acid length of about 30 to about 1000 bp being preferred.

A depolymerizing enzyme is preferably present in an amount sufficient to depolymerize a hybridized target:probe. That amount can vary with the enzyme used, the depolymerization temperature, the buffer, and the like, as are well-known in the art. For a typical reaction carried out in a 20 $\mu$L volume, about 0.25 to about 1 unit (U) of an enzyme such as Klenow exo- is used. About 1 to about 5 U of the thermostable enzymes are used for depolymerization at elevated temperatures.

Other conditions affecting the depolymerization reactions are discussed in the parent applications cited hereinabove, which are incorporated by reference.

It is thus seen that hybridization and depolymerization can lead to the release of an identifier nucleotide or to little or no release of such a nucleotide, depending upon whether the probe:target hybrid is matched or mismatched at the 3'-terminal region. This is also dependent on the type of enzyme used and the type of end, matched or mismatched, that the enzyme requires for depolymerization activity. Exemplary depolymerizing conditions are provided in the Examples that follow, and are expanded upon in the parent application, U.S. patent application Ser. No. 09/358,972, incorporated herein by reference.

The magnitude of a contemplated analytical output under defined conditions is dependent upon the amount of nucleotide released. Where an identifier nucleotide is released, an analytical output can be provided that has a value greater than the background output. Where an identifier nucleotide is not released either because the target sequence was not present in the original sample or because the probe and depolymerizing enzyme chosen do not provide release of a 3'-terminal nucleotide when the target is present, or if the match/mismatch state of the 3'-terminal nucleotide did not match that required for the enzyme used to release a 3'-terminal nucleotide, the analytical output is substantially at a background level.

4. Analytical Output

The analytical output is obtained by detection of the released identifier products, either the released nucleotides or the remainder of the probe. Detection using luminescence spectroscopy, mass spectrometry, fluorescence spectroscopy and absorbance spectroscopy is contemplated. A preferred exemplary detection system is the light emitting luciferase detection system; an exemplary fluorescence detection system is the NADH detection system. These detection systems are discussed hereinbelow.

The fact that nucleotides were released (a qualitative determination), or even the number of nucleotides released (a quantitative determination) can be deduced through examination of the probe after depolymerization. The determination of the size of an oligonucleotide is well known in the art. For example, gel separation and chromatographic separations are well known. Gel imaging techniques are available that take advantage of fluorescence and absorbance spectroscopy as well as radiographic methods. Mass spectrometry of oligonucleotides is also becoming more common.

In some preferred embodiments, ATP is produced via NDPK transfer of a phosphate group from the released identifier nucleotides to added ADP. The resulting ATP is detected by luminescence spectroscopy, fluorescence or absorbance spectroscopy, preferably luminescence spectroscopy. In still another embodiment of the present invention, the pyrophosphate transferring step (pyrophosphorolysis) and the phosphate transferring step (ADP to ATP) are performed in a single pot reaction. In other preferred embodiments, if increased sensitivity is required, the ATP molecules can be amplified through the addition of AMP and adenylate kinase as discussed in the parent applications cited above and incorporated herein by reference.

A. Luminescence Spectroscopic Analysis

Luciferase detection systems are particularly useful for detecting ATP. In the presence of ATP and oxygen, luciferase catalyzes the oxidation of luciferin, producing light that can then be quantified using a luminometer. Additional products of the reaction are AMP, pyrophosphate and oxyluciferin.

In particularly preferred embodiments, ATP detection buffer referred to as L/L reagent (Promega, FF2021) is utilized. Preferably, about 5 to 10 ng of luciferase are used in the reaction. Although it is not intended that the present invention be limited to a specific concentration of luciferase, greater amounts of luciferase have a tendency to increase non-specific background.

It is contemplated that in some embodiments, the dNTPs or NTPs produced by pyrophosphorolysis or nuclease digestion are converted to XTP, which can then be used directly as substrate for luciferase, permitting detection of the nucleic acid. However, the preferred substrate for luciferase is ATP, as demonstrated by Moyer and Henderson, *Anal. Biochem.*, 131:187–89 (1983). When DNA is the initial substrate, an NDPK is conveniently utilized to catalyze the conversion of dNTPs to ATP by the following general reaction:

Reaction 1: dNTP*+ADP→dNDP+ATP* 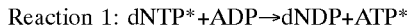

wherein dNTP is a mixture of deoxyribonucleoside triphosphates and dNDP is the corresponding deoxyribonucleoside diphosphate. In Reaction 1, the terminal 5'-triphosphate (P*) of the dNTP is transferred to ADP to form ATP.

Enzymes catalyzing this reaction are generally known as nucleoside diphosphate kinases (NDPKs). NDPKs are ubiquitous, relatively nonspecific enzymes. For a review of NDPKS, see Parks and Agarwal, in *The Enzymes*, Volume 8, P. Boyer ed. (1973).

The use by NDPK of NTPs or dNTPs to convert ADP to ATP is preferably accomplished by adding an NDPK and a molar excess of ADP over the amounts of NTPs or dNTPs expected to be produced by pyrophosphorolysis or nuclease digestion, followed by pyrophosphorylation by PRPP synthetase. The utilization of ADP requires optimization of the amount of ADP added. Too much ADP results in high background levels.

NDPK (EC 2.7.4.6) preparations from several biological sources are commercially available from several suppliers. For example yeast NDPK is available from Sigma Chemical Co., St. Louis, Mo., whereas bovine NDPK is available from ICN Biochemicals, Inc., Costa Mesa, Calif. The particular NDPK selected for most uses described herein is typically a matter of choice. Although yeast, bovine or another NDPK can be used in these reactions, it is preferred to utilize a thermostable NDPK such as the Pfu NDPK along with a thermostable depolymerizing enzyme such as the Tne triple mutant DNA polymerase, Bst DNA polymerase, Ath DNA polymerase, Taq DNA polymerase and Tvu DNA polymerase along with a reaction temperature of about 50° C. to about 90° C. The use of these thermostable enzymes at an above temperature can enhance the sensitivity of the method. The particularly preferred Tne triple mutant DNA polymerase is described in detail in WO 96/41014, whose disclosures are incorporated by reference, and its 610 residue amino acid sequence is provided as SEQ ID NO:35 of that document. That enzyme is referred to in WO 96/41014 as Tne M284 (D323A,D389A). Example 8 illustrates the use of PCR amplification and the Tne triple mutant DNA polymerase in a process of the invention. Example 9 is a multiplex version using the Tne triple mutant DNA polymerase in a process of the invention.

B. Mass Spectrometric Analysis

In one method of the invention, the presence of released nucleotides is analyzed via mass spectrometry. In an embodiment of a method using mass spectrometry, the treated reaction mixture is ionized in a manner such that all components of the treated reaction mixture in the molecular weight range of the released identifier nucleotides and/or the depolymerized probe are measured. Very small differences in molecular weight can be detected using mass spectrographic methods (different isotopes of the same atom are detectable), so any variation from a natural nucleic acid, including a single atom substitution (e.g. a fluorine in place of a hydrogen atom or a replacement of a hydrogen by a deuterium atom) in the identifier nucleotide gives rise to a detectable difference. Nucleic acid analogs used in methods of the invention should not interfere with either the hybridization of the nucleic acid probe or depolymerization of the hybridized probe.

Additionally, mass spectrometry can discriminate between individual nucleotides or nucleosides. For example, if the 3'-identifier nucleotide was a G nucleotide, mass spectrometry can be used to detect the release of that G nucleotide in a method of the present invention. Similarly, mass spectrometry can detect the release of an A, T or C nucleotide, based on the differences in molecular weight of these compounds. Thus, in a multiplexing embodiment of the present invention, mass spectrometry can be used to resolve the presence of one or more 3'-identifier nucleotides, preferably permitting one to distinguish which probe(s) hybridized and were depolymerized.

In a particularly useful aspect of this embodiment, a mass spectral technique referred to as DIOS (desorption/ionization on silicon) was recently reported by Wei et al., *Nature*, 399:243(1999) that can accurately perform one or multiple assays on picogram or attagram amounts using commercially available mass spectrographs adapted with a specialized porous silicon sample well. The older, well known, MALDI mass spectrographic assay or electrospray mass spectrographic assay techniques can also be utilized.

In an embodiment of a multiplex method using mass spectrometry, multiple different identifier nucleotides can be used in the various nucleic acid probes. Using such a technique the presence of the different identifier nucleotides is direct evidence of the presence of the nucleic acid target sequences.

C. Fluorescence Spectroscopic Analysis

A wide variety of fluorescence detection methods can be used herein. In one exemplary contemplated method, an identifier nucleotide includes a fluorescent label. An identifier nucleotide can be fluorescently labeled prior to, or after, release of the identifier nucleotide. In an alternative embodiment when the nucleotide is fluorescently labeled, the analytical output is obtained by mass spectrometry.

In a preferred embodiment of the invention, the fluorescent label is part of a fluorescent analog of a nucleotide. Fluorescent nucleotide analogs are widely known and commercially available from several sources. An exemplary source is NEN™ Life Science Products (Boston, Massachusetts), who offer dideoxy-, deoxy-, and ribonucleotide analogs a labeled with fluorescein, coumarin, tetramethylrhodamine, naphthofluorescein, pyrene, Texas Red®, and Lissamine™. Other suppliers include Amersham Pharmacia Biotech (Uppsala, Sweden; Piscataway, N.J.) and MBI Fermentas, Inc. (Amherst, N.Y.).

An advantage to using fluorescent labels and fluorescence spectroscopy analysis is that there are multiple different labels. Such different labels would be particularly useful in a multiplex embodiment of the invention. Different fluorescent labels would be used in different probes, so that the detection of a particular fluorescently-labeled nucleotide analog as a released identifier nucleotide could be used to deduce which nucleic acid targets are present.

For example, fluorescein has a 488 nm excitation and 520 nm emission wavelength, whereas rhodamine (in the form of tetramethyl rhodamine) has 550 nm excitation and 575 nm emission wavelength. A fluorescence detector provides an excitation source and an emission detector. The emission wavelengths of 520 nm and 575 nm are easily distinguishable using fluorescence spectroscopy.

On a per molecule basis, fluorescence spectroscopy is about 10-fold more sensitive than absorbance spectroscopy. A very wide variety of fluorescence spectroscopy-based detectors are commercially available for reading fluorescence values of single tubes, flow cells and multi-well plates, among others. For example, Labsystems Multiskan models of microplate readers are widely available with a spectral range of 400 to 750 nm, and filters for 340, 405, 414, 450, 492, 540, 620, and 690 nm (e.g. Fisher Scientific, Pittsburgh, Pa.).

It is contemplated that a released identifier nucleotide could be labeled before or after depolymerization using cross-linking chemistry well known in the art with commercially available reagents. For example, fluorescein isothiocyanate and rhodamine B isothiocyanate are both available from Aldrich Chemical Company (Milwaukee, Wis.). References to fluorescein isothiocyanate's use in labeling biological molecules include *Nature*, 193:167 (1962); *Methods Enzymol.* 26:28 (1972); *Anal. Biochem.*, 57:227 (1974); and *Proc. Natl. Acad. Sci., USA,* 72:459 (1975).

It is contemplated that for many embodiments of the invention, it is useful to separate released fluorescent identifier nucleotides from those bound to an oligonucleotide, such as a probe. Thus, the separation techniques well known in the art and discussed above are useful with such an embodiment, including HPLC fitted with a fluorescence detector. The enhanced sensitivity of fluorescence relative to other spectroscopic techniques can be used to increase the sensitivity of a detection or quantification process of the invention.

In the NADH detection system, a combination of two enzymes, phosphoglycerate kinase and glyceraldehyde phosphate dehydrogenase, is used to catalyze the formation of NAD from NADH in the presence of ATP. Because NADH is fluorescent whereas NAD is not, ATP is measured as a loss in fluorescence intensity. Examples of NADH based ATP assays are disclosed in U.S. Pat. Nos. 4,735,897, 4,595,655, 4,446,231 and 4,743,561, and UK Patent Application GB 2,055,200, all of which are herein incorporated by reference.

D. Absorbance Spectroscopic Analysis

An absorbance spectrographic analysis step is contemplated to provide an analytical output, thereby provide for the determination of the presence or absence released identifier nucleotide, and indicate the presence or absence of said nucleic acid target sequence. This embodiment contemplates the chromatographic separation of a reaction mixture that has been treated with a depolymerizing amount of an enzyme whose activity is to release one or more nucleotides from the 3'-terminus of a hybridized nucleic acid.

In an illustrative embodiment, a multiplexed assay for the presence of several different nucleic acid target sequences in a sample is analyzed by absorbance spectroscopy. Several labeled probes to various nucleic acid target sequences are added to a nucleic acid sample. The labels on the probes may be various nucleotide analogs, a different one for each probe. A depolymerizing enzyme is added, such as Klenow exo-, releasing the labeled nucleotides and other nucleotides from the 3'-termini of probes hybridized to target sequences when the 3' terminal nucleotide is matched.

The reaction solution is loaded onto a pre-equilibrated High Pressure Liquid Chromatography (HPLC) column and eluted under conditions that separate the nucleotide analogs from the natural nucleotides. Useful media for chromatographic separation of nucleotides, bases, and nucleosides include reverse phase media, such as a reverse phase C18 column or ODS-80T$_M$ or ODS-120T TSK-GEL by Toso-Haas (Montgomeryville, Pa.), anion exchange media, such as DEAE-25SW or SP-25W TSK-GEL by TosoHaas (Montgomeryville, Pa.), or affinity media, such as Boronate-5PW TSK-GEL by TosoHaas (Montgomeryville, Pa.). Example 5 illustrates an embodiment of the present invention using HPLC.

The HPLC column is fitted with an absorbance detector to monitor the column effluent. Hence, "absorbance spectroscopy" for this type of analysis. Typical wavelengths for monitoring HPLC detection of nucleotides are 250 nm, 260 nm and 280 nm. Such separations of nucleotides and nucleotide analogs are well known in the art. Revich et al., *J. Chromatography*, 317:283–300 (1984), and Perrone & Brown, *J. Chromatography*, 317:301–310 (1984) provide examples of the HPLC separation of dNTPs.

Identification of the separated nucleotide analogs can be accomplished by comparison of the retention times (as monitored by absorbance of effluent at various times) of standards of the nucleotide analogs separated on the same HPLC column under the same conditions. Alternatively, the identity of the nucleotide analogs collected in separate fractions (as determined by continually monitoring the absorbance of the column effluent) can be determined by other standard analytical methods, such as nuclear magnetic resonance or atomic analysis (H,C,N).

In this illustrative example using depolymerization with Klenow exo-, the presence of a released identifier nucleotide from a particular probe indicates the presence of the target sequence that hybridize with that probe.

In an alternative embodiment, the released nucleotides from a depolymerization reaction mixture are separated on a gas chromatograph fitted with an absorbance detector to monitor column effluent.

EXAMPLE 1

Detection of Rolling Circle Amplification Products Obtained After Circularization by Ligation In this example, a probe (oligonucleotide 10367 (SEQ ID NO:7)) is hybridized to either no target, or to a wild type (WT; 8831 (SEQ ID NO:8)) or a mutant (10354 (SEQ ID NO:9)) target and ligated into a circle. An extension probe (10368 (SEQ ID NO:10)) is then hybridized and extended into run-around products, thereby amplifying the target. These products are detected using a complementary probe (10369 (SEQ ID NO:11)) in an interrogation reaction, with relative light unit output being used to distinguish among the possible results. In order to obtain a low, no target, background, it is beneficial to treat the ligation reaction mixture with a combination of exonucleases to remove any DNA that is not circular.

It is seen that the no target reaction gives very low light units and there is about a six fold discrimination between WT and Mutant targets. In these studies, only a single rolling circle extension probe is used and amplification is linear, not exponential. The basis for the WT/Mutant discrimination is whether or not the probe ligates into a circular molecule, because ligation is inefficient at a mismatch position.

One microliter (500 ng) of oligonucleotide 10367 was combined with 1 μL (500 ng) of either oligonucleotide 8831 or 10354 or no target in three separate tubes. Water was added to a final volume of 8 μL. The solutions were heated to 95° C. for 3 minutes, then cooled for 10 minutes at room temperature. One microliter of 10×E. coli ligase buffer (NEB) and 1 μL (10u) E. coli ligase (NEB) were added. The solutions were further incubated for 60 minutes at 37° C. To each solution were then added:

| 0.5 μL | 50 U/μL T7 Gene 6 exonuclease (USB E700254) |
| 0.5 μL | 10 U/μL exonuclease I |
| 2 μl | 10X Thermo Polymerase buffer |
| 7 μL | water |

The solutions were then incubated for 15 minutes at 37° C., followed by 10 minutes at 95° C. To each solution were then added:

| 1 μL | 500 ng/μL 10368 (extension probe (SEQ ID NO:10)) |
| 2 μL | 2 mM dNTPs |

The solutions were heated at 95° C. for 3 minutes, and then cooled for 10 minutes at room temperature to anneal the extension probe. One microliter (8 U) of Bst (LF) DNA polymerase was added and the tubes were incubated at 42° C. for 10 minutes, then 65° C. for 30 minutes to permit extension. One unit of shrimp alkaline phosphatase was added and the tubes were incubated at 37° C. for 30 minutes, and then 65° C. for 15 minutes.

| Master Mix: | |
| --- | --- |
| 10X DNA polymerase buffer | 40 μL |
| 40 mM Sodium Pyrophosphate | 5 μL |
| 10 U/μL Klenow exo- polymerase | 10 μL |
| 1 U/μL NDPK | 4 μL |
| 10 μM ADP | 4 μL |
| Nanopure water | 337 μL |

To proceed with interrogation, the solutions were diluted 1:100 with water and 1 μL of each of the three reactions was combined with 1 μL (500 ng) of interrogation oligonucleotide 10369 and 18 μL water. Each composition so formed was heated at 95° C. for 3 minutes, then cooled for 10 minutes at room temperature. Twenty microliters of master mix were added, and each solution was incubated at 37° C. for 15 minutes. Then, 4 μL of each solution were combined with 100 μL of L/L reagent in duplicate, and light output read in a Turner® TD20/20 luminometer. The results obtained were as shown below.

| Sample | average rlu |
| --- | --- |
| No target | 5.8 |
| WT target | 248.6 |
| Mutant target | 43.5 |

10367
5' ACAACGTCGTGACTAGGATCACGCTAAT-GCTTCAGCCTGATGAGT CCGATCAGCCTGAT-GAGTCCGATCTGGCCGTCGTTTT 3' (circle probe) SEQ ID NO:7

8831 5' CAGTCACGACGTTGTAAAACGACGGCCAGT 3' (WT target) SEQ ID NO:8

10354 5' CAGTCACGACGTTGTGAAACGACGGC-CAGT 3' (mutant target) SEQ ID NO:9

10368 5' AGCATTAGCGTGATCC 3' (rolling circle extension probe) SEQ ID NO:10

10369 5' CAGCCTGATGAGTCCG 3' (circle interrogation probe) SEQ ID NO:11

EXAMPLE 2

Detection of Rolling Circle Amplification Products of M13 DNA

This example uses the pUC/M13 Forward primer (17mer, Promega Q5391) to hybridize to single stranded (ss) M13mp18 DNA and synthesize rolling circle DNA using Bst LF (large fragment) thermostable DNA polymerase. The free nucleotides are then removed with Shrimp Alkaline Phosphatase (SAP) and the rolling circle products detected by pyrophosphorolysis of the probe that is complementary to this product, pUC/M13 primer, reverse (17mer) Promega Q5401.

The following reactions were assembled in duplicate:

| Sample | M13mp18 DNA (μL) | 10X Buffer (μL) | 2 μM dNTPs (μL) | Probe (μL) | Water (μL) |
| --- | --- | --- | --- | --- | --- |
| 1 | 1 (250 ng) | 2 | 2 | none | 14 |
| 2 | 1 (250 ng) | 2 | 2 | 5 | 9 |
| 3 | 1 (250 ng) | 2 | 2 | 5 | 9 |

The assembled solutions were incubated at 95° C. for 3 minutes, then cooled for 10 minutes at room temperature.

To samples 1 and 3, was added 1 μL (8 U) Bst LF DNA polymerase, and all tubes were incubated for 30 minutes at 65° C., then cooled for 2 minutes on ice. One unit of Shrimp Alkaline Phosphatase was added, the solutions incubated at 37° C. for 30 minutes, then heated to 65° C. for 15 minutes to denature the phosphatase enzyme.

One microliter of the reactions was added to 5 μL (50 ng) of pUC/M13 reverse primer, the interrogation oligonucleotide probe, and heated to 95° C. for 3 minutes, then cooled for 10 minutes at room temperature. As in Example 1, twenty microliters master mix were added, and the tubes were heated at 37° C. for 15 minutes. Four microliters were then combined with 100 μL of L/L Reagent, and the light output read on a Turner® TD20/20 luminometer.

| Reaction | Avg. rlu |
|---|---|
| 1. (no extension probe) | 3.5 |
| 2. (no Bst LF DNAP) | 4.1 |
| 3. (complete reaction) | 68.7 |

It can be seen that a signal of about 20 times that of the controls is dependent on the presence of both the Bst (LF) DNA thermopolymerase and the rolling circle extension probe (forward probe).

EXAMPLE 3

Ligase Chain Reaction Prior to Interrogation

In this example, Ligase Chain Reaction (LCR) was performed to amplify wild type and mutant species of the lacI gene fragment used as an amplification control sequence in the LCR kit (Stratagene, 200520) followed by interrogation. LCR is a DNA amplification technique that utilizes a cyclic two-step reaction. Target DNA is denatured at an elevated temperature followed by the annealing of two sets of complementary oligonucleotides to the denatured DNA and their ligation with a thermostable ligase. The ligation products from one cycle serve as targets for the next cycle's ligation reaction.

Oligonucleotide 11192 (SEQ ID NO:12) is complementary to 11195 (WT) (SEQ ID NO:13) and 11196 (mutant) (SEQ ID NO:14). Oligonucleotide 11197 (SEQ ID NO:15) is complementary to 11193 (WT) (SEQ ID NO:16) and 11194 (mutant) (SEQ ID NO:17). The mutant oligonucleotide differs from its counterpart wild type oligonucleotide only at the 3'-terminal base.

The wild type and mutant targets that are present in the LCR kit were used as the targets for the LCR reaction performed according to kit instructions. The LCR product was then quantified and used as the target for interrogation. One microliter of the wild type LCR target (100 pg) was combined with 1 μg of wild type interrogation oligonucleotide (11198 (SEQ ID NO:18)), mutant interrogation oligonucleotide (11199 (SEQ ID NO:19)), or no oligonucleotide along with water to a final volume of 20 μL. A target-only reaction and a probe-only reaction were also assembled as controls. Likewise, similar solutions were assembled with the mutant LCR target. The solutions were heated at 95° C. for 8 minutes to denature the nucleic acid. LCR was performed according to manufacturer's instruction.

The following master mix was assembled.

| | |
|---|---|
| 432 μL | water |
| 120 μL | 10X DNA pol buffer (Promega, M195A) |
| 15 μL | 40 mM NaPPi |
| 15 μL | Klenow exo- (1u/μL) |
| 6 μl | NDPK (1 U/μL) |
| 12 μL | ADP (10 μM) |

Twenty microliters of master mix were added to each solution, and the solutions were further incubated at 37° C. for 15 minutes. Five microliters of each solution were then combined with 100 μL of L/L reagent and light output was measured on a Turners TD20/20 luminometer. The results of average relative light units (Avg. rlu) are shown below:

| | Avg. rlu |
|---|---|
| Wild type target rxns | |
| Probe 11198 (WT) + target | 58.35 |
| Probe 11199 (mutant) + target | 5.29 |
| Probe 11198 only | 2.77 |
| Target only | 3.89 |
| Mutant target rxns | |
| Probe 11198 (WT) + target | 7.78 |
| Probe 11199 (mutant) + target | 77.22 |
| Probe 11199 only | 3.29 |
| Target only | 7.05 |

The data indicate that about 10-fold match/mismatch discrimination can be obtained when performing the interrogation reaction after an LCR amplification reaction.

11192 5' TTGTGCCACGCGGTTGGGAATGTA 3' SEQ ID NO:12

11195 5' TACATTCCCAACCGCGTGGCACAAC 3' SEQ ID NO:13

11196 5' TACATTCCCAACCGCGTGGCACAAT 3' SEQ ID NO:14

11197 5' AACTGGCGGGCAAACAGTCGTTGCT 3' SEQ ID NO:15

11193 5' AGCAACGACTGTTTGCCCGCCAGTTG 3' SEQ ID NO:16

11194 5' AGCAACGACTGTTTGCCCGCCAGTTA 3' SEQ ID NO:17

11198 5' TTTGCCCGCCAGTTGTT 3' SEQ ID NO:18

11199 5' TTTGCCCGCCAGTTATT 3' SEQ ID NO:19

EXAMPLE 4

Amplification-Refractory Mutation System (ARMS) Followed by Interrogation

This example illustrates the detection of nucleic acid produced in ARMS reactions [Newton, C. R. et al., *Nucl. Acids Res.*, 17:2503, (1989)] without running a gel to interpret results. ARMS is based on a PCR probe with a 3' end mismatch at a site of mutation.

In this Example, PCR products are either made or not made with a particular probe depending on the absence or presence of a single base (SNP site) in the target. The probe with a 3'-terminal mismatch cannot amplify the product on the mutant target but can produce a product on the matched wild type target. In this example, unique restriction enzyme sites are built into the PCR probe next to the Pst I restriction site already present in the probes so that the wild type and the mutant products are uniquely identified by the restriction site incorporated. The PCR probes used, 11310 (SEQ ID NO:20), 11311 (SEQ ID NO:21), 11284 (SEQ ID NO:22), 11253 (SEQ ID NO:23), 11255 (SEQ ID NO:24), and 11254 (SEQ ID NO:25), are shown at the end of this example.

Oligonucleotides named 11253 and 11254 were designed and cloned into Promega's pGEM-7zf vector that had been cut with Kpn I and HinD III restriction enzymes. These oligonucleotides contain a short region with a SNP. Clone 53 contains the sequences of oligonucleotides 11284 and 11253. Clone 54 contains the sequences of oligonucleotides 11255 and 11254. The sequences of clones 53 and 54 were confirmed by sequencing. Clones 53 and 54 have a unique EcoR V restriction site that provides a blunt end on cleavage. Clones 53 and 54 were digested to completion with Sca I and then diluted to 1 ng/μL with water prior to use in the following PCR reactions.

PCR Master Mix:

| | |
|---|---|
| 50 μL | 10X Thermophilic buffer |
| 20 μL | 25 mM MgCl$_2$ |
| 10 μL | 10 mM each dNTP |
| 10 μL | 100 μg/mL oligo 11314 |
| 390 μL | water |

The PCR reactions were set up as follows.

| Reaction | Master Mix | Plasmid (1 μL) | Probe (1 μL) |
|---|---|---|---|
| PCR-1 | 48 μL | 53 (WT*) | 11311 (WT) |
| PCR-2 | 48 μL | 53 (WT) | 11310 (Mut*) |
| PCR-3 | 48 μL | 54 (Mut) | 11311 (WT) |
| PCR-4 | 48 μL | 54 (Mut) | 11310 (Mut) |

*WT = wild type;
Mut = mutant

The oligonucleotides used for PCR amplification were 11310 and 11311. Each of those oligonucleotides contains the Pst I restriction enzyme site, as does oligonucleotide 11314. The PCR cycling parameters used were 95° C., 6 minutes. After 4.5 minutes, 1 μL (5u/μL) of Taq DNA polymerase was added, and the reaction mixture was cycled (95° C., 30 seconds; 60° C., 2 minutes)×30; 72° C., 5 minutes.

The four PCR products were digested in standard Pst I restriction enzyme reactions, cleaned with the Wizards PCR DNA Purification System (Promega A7170), and eluted into 50 μL of water. These Pst I-digested PCR products were then cut with either no enzyme, Nco I or Nde I in standard restriction enzyme digest reactions. Reaction 1 of this Example should cut with Nco I, but not with Nde I. Reaction 4 of this Example should cut with Nde I, but not with Nco I.

The following Interrogation Master Mix was assembled.

| | |
|---|---|
| 60 μL | 10X DNA Polymerase buffer |
| 7.5 μL | 40 mM NaPPi |
| 15 μL | 10 U/μL Klenow exo- |
| 6 μL | 1 U/μL NDPK |
| 6 μL | 10 μM ADP |
| 505.5 μL | water |

The following interrogation reactions were assembled, and incubated at 37° C. for 1 hour. Then 1 AL of the reactions was combined with 19 μL of interrogation master mix (in duplicate), incubated for 15 minutes at 37° C. and 5 μL were added to 100 μL of L/L reagent and relative light units (rlu) were measured in a Turners TD20/20 luminometer. The results obtained are shown below.

| Reaction | Second cut DNA | Avg. digest | rlu |
|---|---|---|---|
| 1. | PCR-1 | none | 39.1 |
| 2. | PCR-1 | Nco I | 149.1 |
| 3. | PCR-1 | Nde I | 44.6 |
| 4. | PCR-2 | none | 26.5 |
| 5. | PCR-2 | Nco I | 23.9 |
| 6. | PCR-2 | Nde I | 25.2 |

-continued

| Reaction | Second cut DNA | Avg. digest | rlu |
|---|---|---|---|
| 7. | PCR-3 | none | 28.4 |
| 8. | PCR-3 | Nco I | 26.8 |
| 9. | PCR-3 | Nde I | 27.0 |
| 10. | PCR-4 | none | 43.4 |
| 11. | PCR-4 | Nco I | 54.8 |
| 12. | PCR-4 | Nde I | 116.7 |

PCR-1 is activated for detection by close to four fold by digestion with Nco I but is not activated by digestion with Nde I. PCR-4 is not substantially activated by digestion with Nco I, but is activated close to 3 fold by digestion with Nde I. Neither PCR-2 nor PCR-3 was activated by either enzyme, indicating the absence of product as anticipated.

11310
5' GCTTAAGCTGCAGGGCATATGTGGTGAT-GATATCGTGGGTGAGTTCATTTA 3' SEQ ID NO:20

11311
5' GCTTAAGCTGCAGGGCCATGGTGGTGAT-GATATCGTGGGTGAGTTCATTTT 3' SEQ ID NO:21

11284
5' CTGGAAAATGAACTCACCCACGATATCATCACCA 3' SEQ ID NO:22

11253 5'AGCTTGGTGATGATATCGTGGGTGAGT-TCATTTTCCAGGTAC 3' SEQ ID NO:23

11255 5' CTGGTAAATGAACTCACCCACGATAT-CATCACCA 3' SEQ ID NO:24

11254 5' AGCTTGGTGATGATATCGTGGGTGAGT-TCATTTACCAGGTAC 3' SEQ ID NO:25

EXAMPLE 5
Restriction Enzyme Digestion Prior to Interrogation

This Example concerns the use of two synthetic targets generated by PCR amplification with Pst I restriction enzyme sites on the probes. These targets are first digested with Pst I, which leaves 3' overhangs on both ends, making the products refractory to detection by means of interrogation using a Klenow exo- enzyme. The two PCR products differ in the presence of another unique restriction enzyme site. The ends generated by this second digest provide ends that have a 5' overhang and are permissive for interrogation.

Oligonucleotides 11315 (SEQ ID NO:26) and 11314 (SEQ ID NO:27) both contain a Pst I restriction enzyme site (CTGCAG) near the 5' end preceded by six arbitrary bases to permit efficient digestion. These oligonucleotides were used to create PCR products, about 200 base pairs in size, using the vectors pGEM-7zf(+) and pGEM-9zf(-) (Promega, P2251 and P2391, respectively) for targets and using standard PCR conditions.

Forty microliters (800 ng) of each PCR product were digested with Pst I restriction enzyme to completion and again purified with Wizard™ PCR DNA Purification System to remove the small digested fragment. Then the two different PCR products were further digested in separate reactions with BamH I, Spe I and EcoR I enzymes or with no additional enzyme. BamH I digests only the PCR product from pGEM-7zf(+) (PCR-1); Spe I digests only the PCR product from pGEM-9zf(-) (PCR-2); and EcoR I digests both PCR products. All three of these enzymes leave a 5' overhang that is responsive to interrogation.

Four microliters of the Pst I digested DNA was digested with the second enzyme, diluted two fold, and one microliter was combined with 19 μL master mix and incubated for 15 minutes at 37° C. Five microliters thereafter were added to 100 μL of L/L reagent and relative light units (rlu) read on a Turner® TD20/20 luminometer to provide the data (in duplicate) in the table below, thereby illustrating interrogations for the presence or the absence of the second digestion.

| Master Mix: | |
|---|---|
| 10X DNA polymerase buffer | 40 μL |
| 40 mM Sodium Pyrophosphate | 5 μL |
| 10 U/μL Klenow exo- pol. | 10 μL |
| 1 U/μL NDPK | 4 μL |
| 10 μM ADP | 4 μL |
| Nanopure water | 337 μL |

| Reaction | DNA | Second/enzyme digestion | Avg. rlu |
|---|---|---|---|
| 1. | PCR-1 | none | 38.9 |
| 2. | PCR-1 | BamH I | 325 |
| 3. | PCR-1 | Spe I | 62.2 |
| 4. | PCR-1 | EcoR I | 386.9 |
| 5. | PCR-2 | none | 26.4 |
| 6. | PCR-2 | BamH I | 37.3 |
| 7. | PCR-2 | Spe I | 265.3 |
| 8. | PCR-2 | EcoR I | 302.2 |

The PCR-1 product contains a BamH I and an EcoR I site, but no Spe I site and responds appropriately. The PCR-2 product contains a Spe I and an EcoR I site, but no BamH I site and also responds appropriately.

These data demonstrate that detection was stimulated about 10 fold by digestion with the appropriate enzyme. Furthermore, multiplexing was simulated by mixing the two PCR fragments together and detecting only one of them by digestion with the appropriate enzyme followed by interrogation. This method can thus be used to detect a single nucleotide polymorphism that destroys or creates a restriction site without running a gel.

11315 5' ATGATGCTGCAGCAGGAAACAGCTATGAC 3' SEQ ID NO:26

11314 5' ATGATGCTGCAGGTTTTCCCAGTCACGAC 3' SEQ ID NO:27

EXAMPLE 6
Multiplex Determination of Nucleotide Sequences Associated with Factor V Leiden and with a Prothrombin SNP in the Same Reaction An assay was performed in this example to determine if a human DNA sample contains the Leiden mutation of the Factor V gene, as well as a particular Prothrombin single nucleotide polymorphism (SNP). The assay for these two characteristics is performed simultaneously in the same reaction.

Primers PT5 (SEQ ID NO:28) and PT6 (SEQ ID NO:29) were used to PCR-amplify a region of human genomic DNA spanning about 500 base pairs encoding the prothrombin gene. Primers 10861 (SEQ ID NO:30) and 9828 (SEQ ID NO:31) were used to PCR amplify a region of human genomic DNA spanning about 300 base pairs encoding the Factor V gene. Probes PT5 and 10861 have phosphorothioate linkages between the first five bases at the 5' end.

The Factor V and Prothrombin fragments were co-amplified in one PCR reaction under the following conditions:

| 5 μL | 10X PCR buffer |
|---|---|
| 5 μL | 25 mM MgCl$_2$ |
| 1 μL | 10 mM dNTPs |
| 1 μL | primer PT5 (50 pmol) |
| 1 μL | primer PT6 (50 pmol) |
| 1 μL | primer 10861 (50 pmol) |
| 1 μL | primer 9828 (50 pmol) |
| 1 μL | Human genomic DNA (40 ng) |
| 36 μL | water |
| 1.25 U | Taq |

The PCR cycling parameters were as follows: 94° C., 2 minutes; (94° C., 30 seconds; 60° C., 1 minutes; 70° C., 1 minutes)×40; 70° C., 5 minutes. Fifty units of T7 gene 6 Exonuclease (USB Amersham) were added to 25 μL of the PCR reaction and the solution was incubated for 30 minutes at 37° C. Magnetic silica (Promega, A1330) was used to remove free nucleotides from the solution and the remaining DNA was eluted with 100 μL of water.

The Prothrombin interrogation probes used are 11265 (SEQ ID NO:32) that matches mutant prothrombin sequence and 11266 (SEQ ID NO:33) that matches wild type prothrombin sequence. Each of those probes has a destabilizing mutation eight bases from the 3' end so that complete complementarity cannot be present between the probe and target sequences. The Factor V interrogation probes used are 9919 (SEQ ID NO:34) that matches wild types Factor V sequence and 11432 (SEQ ID NO:35) that matches Factor V Leiden mutation sequence.

Four microliters of the eluted DNA were interrogated with each interrogation probe independently and also with the Factor V and Prothrombin mutant probes conjointly in one reaction. The interrogation reactions were assembled as follows.

| 4 μL | DNA (PCR product, Exo6 treated and purified) |
|---|---|
| 150 pmol | each interrogation oligo |
| water | added to a final volume of 20 μL |

The reactions were incubated at 95° C. for 3 minutes and then at 37° C. for 10 minutes. Twenty microliters of the standard master mix was then added and the reaction incubated at 37° C. for 15 minutes. One hundred microliters of the L/L reagent were then added and the light output measured in a Turner® TD20/20 luminometer. The master mix contains the following.

| 71 μL | water |
|---|---|
| 20 μL | 10X DNA pol buffer |
| 5 μL | 40 mM NaPPi |
| 2 μL | 10 μM ADP |
| 1 μL | 1 unit/μL NDPK |
| 1 μL | 10 unit/μL Klenow exo- |

The light output was as follows.

| Interrogation oligo | Genomic DNA 1 | Genomic DNA 2 |
|---|---|---|
| 9919 (FV wt) | 431 | 424 |
| 11432 (FV mut) | 45 | 57 |
| 11266 (Pt wt) | 902 | 878 |
| 11265 (Pt mut) | 145 | 161 |

-continued

| Interrogation oligo | Genomic DNA 1 | Genomic DNA 2 |
|---|---|---|
| 11432 + 11265 | 77 | 98 |
| no oligo | 44 | 57 |

These data indicate that the both genomic DNAs are from individuals wild type for Factor V and for wild type Prothrombin.

An additional 96 clinical genomic DNA samples were interrogated as described above. All the data fit into the following equation for calling the genotype.

$$\frac{rlu \text{ both wild type probes}}{rlu \text{ both wild type} + rlu \text{ both mutant probes}} > 0.75$$

This equation is the analytical output from the interrogation including both wild type probes divided by the analytical output from both wild type probes added to the analytical output from both mutant probes. If that value is greater than 0.75 then the sample is homozygous wild type at both loci. If that value is less than 0.75 then there is good likelihood that at least one allele at least one of the loci is mutant and the sample should be further analyzed for the genotype at each locus separately.

PT5 5' ATAGCACTGGGAGCATTGAGGC 3' SEQ ID NO:28
PT6 5' GCACAGACGGCTGTTCTCTT 3' SEQ ID NO:29
10861 5' TGCCCAGTGCTTAACAAGACCA 3' SEQ ID NO:30
9828 5' TGTTATCACACTGGTGCTAA 3' SEQ ID NO:31
11265 5' GTGATTCTCAGCA 3' SEQ ID NO:32
11266 5' GTGATTCTCAGCG 3' SEQ ID NO:33
9919 5' GACAAAATACCTGTATTCCTCG 3' SEQ ID NO:34
11432 5' GACAAAATACCTGTATTCCTTG 3' SEQ ID NO:35

EXAMPLE 7
Dual Probe Rolling Circle Amplification Prior to Interrogation

The amplification of target nucleic acid by means of rolling circle amplification prior to the interrogation reaction is examined in this Example as a substitute methodology for PCR amplification. A typical rolling circle amplification of a circular target using two probes is described in Lizardi, P. M. et al., *Nature Genetics*, 19:227 (1998).

The wild type target used in this study is oligonucleotide 10870 (SEQ ID NO:3). The mutant target used is oligonucleotide 10994 (SEQ ID NO:4). The open circle probe which anneals to the targets is oligonucleotide 10865 (SEQ ID NO:1). Rolling circle replication primer which anneals to the open circle probe is oligonucleotide 10866 (SEQ ID NO:2). Rolling circle replication primer 10869 (SEQ ID NO:5) has a 3'-terminal residue that anneals only to the wild type target, whereas probe 10989 (SEQ ID NO:6) has a 3'-terminal residue that anneals only to the mutant target. Probes 10869 and 10989 both have a nucleotide located 3 nucleotides from the 3'-terminal nucleotide that is not complementary to either the wild type or the mutant target. This mismatched base was intentionally incorporated to provide for increased specificity in the interrogation reaction.

This Example uses a synthetic heterozygote solution containing both the 10870 and 10994 oligonucleotides as targets. The 10865 oligonucleotide anneals to both of these targets in a similar manner, forming a circular target with a seven base pair gap that needs to be filled in from the 10865 3' end and ligated in order for complete rolling circle amplification to proceed. The annealing of the 10865 oligonucleotide to 10870 wild type and 10994 mutant oligonucleotides is diagrammed in FIG. 1. In the absence of ligation, no priming can occur.

The following heterozygote solution was assembled:

| 2 µL | 10X ampligase buffer (Epicenter) |
|---|---|
| 2 µL | 2 mM dTTP, dCTP, dATP |
| 1 µL | 500 µg/mL probe 10865 (probe) |
| 0.5 µL | 500 µg/mL probe 10870 (wild type target strand) |
| 0.5 µL | 500 µg/mL probe 10994 (mutant target strand) |
| 1 µL | 5 u/µL Tfl DNA polymerase |
| 1 µL | 5 u/µL Ampligase (Thermostable ligase, Epicenter) |
| 12 µL | water |

Likewise, the homozygote solutions were assembled using either 1 µL probe 10870 and no 10994 to prepare the wild type homozygote target, or no 10870 and 1 µL 10994 to prepare the mutant homozygote target. Only three deoxynucleotides are included in the solutions to prevent strand displacement. The solutions were incubated at 65° C. for 30 minutes after which time they were estimated to have formed about $2.5 \times 10^{11}$ circular molecules per microliter. After the 30 minutes of incubation they were diluted to about 2500 circular targets per microliter. The heterozygote, the homozygote wild type and homozygote mutant gap-fill ligations were then used to assemble the following amplification reactions.

| Reaction: | 1 | 2 | 3 | 4 | 5 | 6 |
|---|---|---|---|---|---|---|
| 1 µL Target | WT* homoZ* | WT homoZ | Mut* homoZ | Mut homoZ | heteroZ* | heteroZ |
| 0.5 µL Probe | 10869 WT | 10989 Mut | 10869 WT | 10989 Mut | 10869 WT | 10989 Mut |

*WT = wild type; Mut = mutant; homoZ = homozygote; and heteroZ = heterozygote

Additionally, each tube contained 2 µL 10×Polymerase buffer, 1 µL 10 mM dNTPs, 0.5 µL probe 10866, 1 µL 1.2 µg/µL T4 Gene 32, 1.5 µL DMSO and 18.5 µL water. The assembled components were then put on ice and 3 µL Vent exo- (2 U/µL) were added. The solutions were covered with 30 µL of mineral oil and placed at 95° C. for 3 minutes then 65° C. for 90 minutes. The free nucleotides were then removed using the Wizard™ PCR purification system (Promega, A7170) and the DNA eluted with 50 µL water.

The following Master mix was assembled.

| 30 µL | 10X Buffer A |
|---|---|
| 3.75 µL | 40 mM NaPPi |
| 15 µL | T4 DNA polymerase (10 U/µL) |
| 3 µL | NDPK (1 U/µL) |
| 3 µL | 10 µM ADP (Sigma) |
| 245 µL | water |

One microliter of the above amplification reactions was added to 19 µL master mix in duplicate tubes. The tubes were incubated for 15 minutes at 37° C., then 5 µL of the reaction were added to 100 μL of L/L reagent (Promega F202A) and light output was measured in a Turner® TD20/20 luminometer.

| Rxn* | Relative light units | | Second probe | Target |
|---|---|---|---|---|
| | Undiluted target | 1:4 diluted target | | |
| 1. | 618.6 | 458.2 | WT* | WT homoZ* |
| 1. | 621.6 | 457.7 | WT | WT homoZ |
| 2. | 282.4 | 90.2 | Mut* | WT homoZ |
| 2. | 288.4 | 100.3 | Mut | WT homoZ |
| 3. | 365.9 | 148.6 | WT | Mut homoZ |
| 3. | 379.8 | 149.9 | WT | Mut homoZ |
| 4. | 632.5 | 461.5 | Mut | Mut homoZ |
| 4. | 650.2 | 442.4 | Mut | Mut homoZ |
| 5. | 606.1 | 381.1 | WT | heteroZ* |
| 5. | 608.6 | 394.3 | WT | heteroZ |
| 6. | 631.0 | 420.1 | Mut | heteroZ |
| 6. | 637.3 | 411.4 | Mut | heteroZ |

*Rxn = reaction; WT = wild type; Mut = mutant; homoZ = homozygote; and heteroZ = heterozygote At the lower amount of target DNA, the mutant:wild type discrimination improves to 3–5 fold from the 2–fold exhibited when using the undiluted target DNA. This indicates that the study using the undiluted target was likely out of the linear range. The heterozygote ratio for both studies is close to the expected 1:1.

10870 5'TTGCAGAGAAAGACAATATAGTTCTTG-GAGAAGGTGGAATCACACTGAGTGGA 3' SEQ ID NO:3

10994 5'TTGCAGAGAAAGACAATATAGT-TCTTTGAGAAGGTGGAATCACACTGAGTGGA 3' SEQ ID NO:4

10865 5'GAACTATATTGTCTTTCTCTGATTCT-GACTCGTCATGTCTCAGCTTTAGTT-TAATACGACTCACTATAGGGCTCAGTGT-GATTCCACCT 3' SEQ ID NO:1

10866 5' CTAAAGCTGAGACATGACGAGTC 3' SEQ ID NO:2

10869 5' CTCAGTGTGATTCCACCTTCACC 3' SEQ ID NO:5

10989 5' CTCAGTGTGATTCCACCTTCACA 3' SEQ ID NO:6

EXAMPLE 8

Tne Triple Mutant Tne Polymerase and Thermostable NDPK Used to Interrogate Congenital Adrenal Hyperplasia Congenital adrenal hyperplasia (CAH) is a group of autosomal recessive diseases resulting from a wide range of mutations in the steroid 21-hydroxylase (CYP21) gene that contains 10 exons. There is a high level of nucleic acid homology (98% in exons, 96% in introns) between CYP21, the functional gene, and CYP21P, the nonfunctional pseudogene. The many types of mutations in this gene that can lead to disease include complete gene deletions, large gene conversions, single point mutations, and a small 8bp deletion [See, White, et al., Hum. Mutat., 3:373–378 (1994)].

The majority of the CAH disease-causing mutations are sequences present in the nonexpressed CYP21P pseudogene, and arise in the CYP21 gene through recombination between CYP21P and CYP21. Thus, one mutation detection strategy specifically detects the CYP21 gene, and not the CYP21P pseudogene. The frequency of disease-carrying alleles in the population is about 1 in 50.

In this example, the CAH target was interrogated for a variety of mutations using Klenow exo- and yeast NDPK, and the results were compared to a similar analysis using Tne triple mutant thermostable DNA polymerase and a thermostable Pfu NDPK. Both wild type CAH PCR products, mutant synthetic targets, and a pseudogene PCR product amplified from the cloned CYP21P pseudogene were utilized as targets in this assay. They are listed below.

Primer pairs used in PCR amplification and the resulting products are as follows.

| Primers | Size PCR Segment | Segment Amplified |
|---|---|---|
| 10912 + 10909 | 1400 bp | 5' end CYP21 |
| 11461 + 11480 | 918 bp | 5' end CYP21 |
| 10910 + 11286 | 1492 bp | 3' end CYP21 |
| 11535 + 11286 | 1496 bp | 3' end CYP21 |
| 10912 + 10911 | 2680 bp | pseudogene (CYP21P) |

Synthetic targets and interrogation oligos utilized are listed below.

PCR reactions were assembled to amplify regions of the CAH gene with 4 different probe sets, using undigested human genomic DNA (Promega, G3041) as target (25 ng per reaction). For amplification of the pseudogene, human genomic DNA was predigested with the restriction enzyme Bcl I, which specifically cleaves the CYP21 gene upstream of the forward PCR probe, thus permitting only amplification of CYP21P [Krone, Clinical Chem. 44(10):2075–2082 (1998)].

The 2680 bp PCR product was amplified from 50 ng of digested DNA and subsequently cloned into the plasmid vector PGEM-T Easy (Promega, A1380) following the manufacturer's protocol. A clone was selected and sequenced (USB Sequenase kit, US70770) to confirm it was indeed the pseudogene. The cloned CYP21P gene in the pGEM-T Easy vector was used in subsequent amplifications to obtain pure pseudogene PCR product for mutation interrogation analysis (100 pg of plasmid per PCR reaction).

All 50 μL amplification reactions contained the following reagents: genomic DNA (as described above), 1X reaction buffer (M1901), 1.0–1.5 mM magnesium chloride (all with 1.0 mM except probe pair 10912+10911 for pseudogene, which contained 1.5 mM MgCl$_2$; Promega, A3511), 200 μM each dNTP (C1141), 50 pmoles each probe, and 2.5 units Taq DNA Polymerase (M1665).

The following cycling profile was utilized for all amplifications: 5 minutes at 95° C.; 40 cycles of 30 seconds at 94° C., 1 minute at 55° C., 1 minute per kbp of product at 72° C.; 8 minutes at 68° C.; soak at 4° C. The products were analyzed on 1% agarose gels and compared to DNA molecular weight standards to confirm product sizes were correct. An aliquot of each PCR reaction (25 μL) was then treated with 50 units T7 Gene6 Exonuclease (USB, E70025Y) for 15 minutes at 37° C., followed by purification using the Wizard™ PCR Prep DNA Purification System (Promega, A7170) with 3×1 mL 80% isopropanol washes. The exonuclease-treated DNA was eluted in 100 μL of nuclease-free water.

Each interrogation assay (20 μL total volume) contained 4 μL of purified PCR product or 5 ng of synthetic target, and 1 μg interrogation oligo probe (or water for the no-oligo background control). The reactions were incubated at 95° C. for 3 minutes, followed by 10 minutes at 37° C. for Klenow exo- or 55° C. for Tne polymerase. Twenty microliters of master mix were added (2 mM sodium pyrophosphate, 0.2 pM ADP, 2×polymerase buffer (M195A for Klenow or M1901 for Tne), 5 mM magnesium chloride for Tne only, 1–2 U Klenow exo- and 0.2 U yeast NDPK or 1 U Tne triple mutant polymerase and 0.1 U Pfu NDPK) and the reaction incubated 15 minutes at 37° C. (Klenow exo-) or 55° C. (Tne). The entire reaction was then added to 100 μL of L/L reagent (Promega FF202A) and light output read in a Turners TD20/20 luminometer.

Although 55° C. was used in these studies with the Tne triple mutant polymerase and the Pfu NDPK, higher temperatures can also be used. The 55° C. temperature selected appeared to be a good compromise between interrogation oligo annealing and enzymatic activity. Thus, higher incubation temperatures can be beneficial if longer interrogation oligos are utilized.

The table below contains the relative light units (rlu) obtained. The data represent the combined results of many separate studies using the various enzymes. The use of the Tne triple mutant polymerase and Pfu NDPK particularly improved the discrimination ratio for the CAH wild type PCR products at mutation sites 2 and 6, whereas the thermostable enzymes improved the discrimination ratio for the mutant pseudogene PCR product at mutation sites 3, 4, and 5. The synthetic targets worked well with both enzymes, however the signals and discrimination ratios were higher for the thermostable enzymes at almost all of the mutation sites.

| Target DNA | Klenow/ NDPK No oligo | Klenow/ NDPK WT oligo | Klenow/ NDPK Mutant oligo | Tne/ Pfu NDPK No oligo | Tne/ Pfu NDPK WT* oligo | Tne/ Pfu NDPK Mutant oligo | Mut* Site |
|---|---|---|---|---|---|---|---|
| CAH WT 1400 bp | 176.9 | 1050.0 | 204.0 | | | | 1 |
| CAH WT 1400 bp | 176.9 | 1149 | 625.5 | | | | 2 |
| CAH WT 1492 bp | 388.9 | 496.2 | 414.7 | | | | 3 |
| CAH WT 1492 bp | 388.9 | 881.4 | 383.9 | | | | 4 |
| CAH WT 1492 bp | 388.9 | 940.3 | 477.3 | | | | 5 |
| CAH WT 1492 bp | 388.9 | 205.2 | 207.0 | | | | 6 |
| CAH WT 918 bp | | | | 129.4 | 443.0 | 125.6 | 1 |
| CAH WT 918 bp | | | | 129.4 | 440.9 | 134.7 | 2 |
| CAH WT 1496 bp | | | | 124.3 | 261.6 | 118.3 | 3 |
| CAH WT 1496 bp | | | | 124.3 | 259.4 | 121.7 | 4 |
| CAH WT 1496 bp | | | | 124.3 | 276.3 | 135.6 | 5 |
| CAH WT 1496 bp | | | | 124.3 | 214.0 | 112.3 | 6 |
| CAH WT 1496 bp | | | | 124.3 | 252.5 | 174.5 | 7 |
| Pseudo-gene 2680 bp | 15.89 | 115.7 | 109.2 | 176.1 | 419.0 | 537.3 | 1 |
| Pseudo-gene 2680 bp | 15.89 | 45.29 | 140.4 | 176.1 | 388.6 | 397.5 | 2 |
| Pseudo-gene 2680 bp | 15.89 | 129.6 | 141.6 | 176.1 | 477.8 | 772.5 | 3 |
| Pseudo-gene 2680 bp | 15.89 | 63.34 | 149.2 | 176.1 | 369.4 | 999.7 | 4 |
| Pseudo-gene 2680 | 15.89 | 115.8 | 91.28 | 1676.1 | 412.1 | 945.9 | 5 |

-continued

|  | Klenow/ NDPK | Klenow/ NDPK | Klenow/ NDPK | Tne/ Pfu NDPK | Tne/ Pfu NDPK | Tne/ Pfu NDPK |  |
|---|---|---|---|---|---|---|---|
| bp Pseudo-gene 2680 bp |  |  |  | 176.1 | 202.7 | 945.0 | 7 |
| Synthetic Temp. 1 * | 95.65 | 128.2 | 831.2 | 56.92 | 76.58 | 1499 | 1 |
| Synthetic Temp. 2 | 81.09 | 119.3 | 774.9 | 58.46 | 171.8 | 1521 | 2 |
| Synthetic Temp. 3 | 83.22 | 315.6 | 1496 | 54.05 | 171.2 | 2206 | 3 |
| Synthetic Temp. 4 | 87.71 | 85.82 | 1199 | 55.29 | 152.1 | 2829 | 4 |
| Synthetic Temp. 5 | 78.80 | 332.5 | 1071 | 57.49 | 76.91 | 837.7 | 5 |
| Synthetic Temp. 6 | 79.86 | 57.0 | 322.0 | 56.68 | 140.6 | 2328 | 6 |
| Synthetic Temp. 7 | 86.99 | 1738 | 1285 | 209.2 | 4162 | 351.3 | 2 |
| Synthetic Temp. 8 | 98.50 | 1005 | 29.24 | 212.2 | 2121 | 260.4 | 6 |

*WT = wild type; Mut = mutation; Temp. = template

PCR Primers Utilized:
10909 5' CCAGAGCAGGGAGTAGTCTC 3' SEQ ID NO:36 CAH reverse primer; 5' most 3 linkages phosphorothioate (CYP21 only)
10912 5' GCATATAGAGCATGGCTGTG 3' SEQ ID NO:37 CAH forward primer
10910 5' CCTGTCCTTGGGAGACTAC 3' SEQ ID NO:38 CAH forward primer (CYP21 only)
10911 5' CCCAGTTCGTGGTCTAGC 3' SEQ ID NO:39 CAH reverse primer; 5' most 3 linkages phosphorothioate
11286 5' TCCTCACTCATCCCCAAC 3' SEQ ID NO:40 CAH reverse primer; 5' most 3 linkages phosphorothioate
11461 5'GAAATACGGACGTCCCAAGGC 3' SEQ ID NO:41 CAH forward primer
11480 5' CTTTCCAGAGCAGGGAGTAG 3' SEQ ID NO:42 CAH reverse primer; 5' most 3 linkages phosphorothioate (CYP21 only)
11535 5' CCGGACCTGTCCTTGGGAGA 3' SEQ ID NO:43 CAH forward primer (CYP21 only)

Synthetic Targets Utilized:
11293 5' AGAAGCCCGGGGCAAGAGGCAGGAGGTG-GAGGCTCCGGAG 3' SEQ ID NO:44
 CAH Synthetic Target 1 for Interrogator oligo 1 (pseudogene/mutant—exon 1)
 Mutation site 1
11294 5' AGCTTGTCTGCAGGAG-GAGCTGGGGGCTGGAGGGTGGGAA 3' SEQ ID NO:45
 CAH Synthetic Target 2 for Interrogator oligo 2 (pseudogene/mutant—intron 2)
 Mutation site 2
11295 5' TCCGAAGGTGAGGTAACAGTTGATGCTG-CAGGTGAGGAGA 3' SEQ ID NO:46
 CAH Synthetic Target 3 for Interrogator oligo 3 (pseudogene/mutant—exon 4)
 Mutation site 3
11296 5' TCCACTGCAGCCATGTGCAAGTGCCCT-TCCAGGAGCTGTC 3' SEQ ID NO:47
 CAH Synthetic Target 4 for Interrogator oligo 4 (pseudogene/mutant—exon 7)
 Mutation site 4
11297 5' TCGTGGTCTAGCTCCTCCTACAGTCGCT-GCTGAATCTGGG 3' SEQ ID NO:48
 CAH Synthetic Target 5 for Interrogator oligo 5 (pseudogene/mutant—exon 8)
 Mutation site 5
11298 5' GCTAAGGGCACAACGGGCCACAGGCG-CAGCACCTCGGCGA 3' SEQ ID NO:49
 CAH Synthetic Target 6 for Interrogator oligo 12 (pseudogene/mutant—exon 8)
 Mutation site 6
11484 5' CAGCTTGTCTGCAGGAGGAGT-TGGGGGCTGGAGGGTGGGA 3' SEQ ID NO:50
 CAH Synthetic Target 7 for Interrogator oligo 7 (wild type—intron 2)
 Mutation site 2
11485 5'GGCTAAGGGCACAACGGGCCGCAGGCG-CAGCACCTCGGCG 3' SEQ ID NO:51
 CAH Synthetic Target 8 for Interrogator oligo 11 (wild type—exon 8)
 Mutation site 6

Interrogation Oligos Probes Utilized:
11143 5' CGGAGCCTCCACCTCCCG 3' SEQ ID NO:52
 CAH interrogator oligo 6 (wild type) for mutation site 1
11085 5' CACCCTCCAGCCCCCAGC 3' SEQ ID NO:53
 CAH interrogator oligo 2 (pseudogene/mutant) for mutation site 2

11084 5' CGGAGCCTCCACCTCCTG 3' SEQ ID NO:54 CAH interrogator oligo 1 (pseudogene/mutant) for mutation site 1

11086 5' CCTCACCTGCAGCATCAAC 3' SEQ.ID NO:55 CAH interrogator oligo 3 (pseudogene/mutant) for mutation site 3

11144 5' CACCCTCCAGCCCCCAAC 3' SEQ ID NO:56 CAH interrogator oligo 7 (wild type) for mutation site 2

11145 5' CCTCACCTGCAGCATCATC 3' SEQ ID NO:57 CAH interrogator oligo 8 (wild type) for mutation site 3

11087 5' CCTGGAAGGGCACTT 3' SEQ ID NO:58 CAH interrogator oligo 4 (pseudogene/mutant) for mutation site 4

11146 5' CCTGGAAGGGCACGT 3' SEQ ID NO:59 CAH interrogator oligo 9 (wild type) for mutation site 4

11088 5' GATTCAGCAGCGACTGTA 3' SEQ ID NO:60 CAH interrogator oligo 5 (pseudogene/mutant) for mutation site 5

11147 5' GATTCAGCAGCGACTGCA 3' SEQ ID NO:61 CAH interrogator oligo 10 (wild type) for mutation site 5

11287 5' CGAGGTGCTGCGCCTGCG 3' SEQ ID NO:62 CAH interrogation oligo 11 (wild type) for mutation site 6

11288 5' CGAGGTGCTGCGCCTGTG 3' SEQ ID NO:63 CAH interrogation oligo 12 (pseudogene/mutant) for mutation site 6

11641 5'GGGATCACATCGTGGAGATG 3' SEQ ID NO:64 CAH interrogation oligo 23 (wild type) for mutation site 7

11642 5'GGGATCACAACGAGGAGAAG 31 SEQ ID NO:65 CAH interrogation oligo 24 (pseudogene/mutant) for mutation site 7

EXAMPLE 9

Multiplex Analysis of Congenital Adrenal Hyperplasia (CAH) Gene

The use of thermostable enzymes to interrogate the CAH gene, as described in Example 8, has also permitted the interrogation of up to 6 multiple sites within one reaction. The method used in this Example is illustrative of routine studies carried out in screening laboratories where usual results show the presence of an expected gene (or the absence of a mutant gene) in almost all of the samples, and only rarely shows the presence of a mutant gene. In the case illustrated here, a qualitative result is provided from which the exact mutation present can be determined in a subsequent assay.

Thus, equal volumes of the CAH wild type (WT) 918 bp and 1496 bp PCR products (see Example 8) were combined (to thus span the entire CAH gene) and interrogated either separately at each mutation site, or as a multiplexed group. The discrimination ratio was good both in the separate reactions for the combined PCR products, as well as the multiplexed reaction. In addition, the multiplexed reaction using the CAH wild type PCR products and either 6 wild type interrogation oligo probes or 6 mutant interrogation oligo probes was combined with an equimolar amount of synthetic target (mutant synthetic target for each mutation site; 0.2 pmoles either PCR product or synthetic target), to simulate a heterozygote sample.

| Target DNA | Tne/Pfu NDPK, No Oligo | Tne/Pfu NDPK, WT Oligo | Tne/Pfu NDPK Mutant Oligo | Probe for Mutation Site | Mutant Synthetic Target Added |
|---|---|---|---|---|---|
| CAH WT 918 bp + 1496 bp | 172.7 | 553.0 | 180.2 | 1 | |
| Same | 172.7 | 535.7 | 184.0 | 2 | |
| Same | 172.7 | 494.8 | 182.0 | 3 | |
| Same | 172.7 | 486.7 | 148.7 | 4 | |
| Same | 172.7 | 471.7 | 187.9 | 5 | |
| Same | 172.7 | 317.5 | 179.7 | 6 | |
| Same | 172.7 | 297.5 | 246.4 | 7 | |
| Same | 523.7 | 1929.0 | 499.5 | 1, 2, 3, 4, 5 and 6 | |
| Same | 506.0 | 1882.0 | 2234.0 | 1 | 1 |
| Same | 525.4 | 1848.0 | 1505.0 | 2 | 2 |
| Same | 535.9 | 1735.0 | 2877.0 | 3 | 3 |
| Same | 547.5 | 1880.0 | 4879.0 | 4 | 4 |
| Same | 552.4 | 2000.0 | 3864.0 | 5 | 5 |
| Same | 482.9 | 1938.0 | 2189.0 | 6 | 6 |
| Same | 514.5 | 1791.0 | 4192.0 | 2 + 4 | 2 + 4 |
| Same | 537.6 | 1752.0 | 3427.0 | 5 + 6 | 5 + 6 |

Because of the large size of the CAH gene and the large number of different mutations that may be present, the use of the thermostable enzymes, and thus the increased stringency of the detection procedure, was found to be highly advantageous with this complex target. Mutation sites that interrogated poorly using Klenow exo- and yeast NDPK at 37° C., were more successfully interrogated when using the Tne triple mutant polymerase and Pfu NDPK at elevated temperatures. In addition, use of the thermostable enzymes permitted the multiplexing of numerous wild type or mutant interrogation oligos in the same interrogation assay, to obtain the rapid screening for mutations that may be present.

11143 5' CGGAGCCTCCACCTCCCG SEQ ID NO:52 CAH interrogator oligo 6 (wild type) for mutation site 1

11085 5' CACCCTCCAGCCCCCAGC 3' SEQ ID NO:53 CAH interrogator oligo 2 (pseudogene/mutant) for mutation site 2

11084 5' CGGAGCCTCCACCTCCTG 3' SEQ ID NO:54 CAH interrogator oligo 1 (pseudogene/mutant) for mutation site 1

11086 5' CCTCACCTGCAGCATCAAC 3' SEQ ID NO:55 CAH interrogator oligo 3 (pseudogene/mutant) for mutation site 3

11144 5' CACCCTCCAGCCCCCAAC 3' SEQ ID NO:56 CAH interrogator oligo 7 (wild type) for mutation site 2

11145 5' CCTCACCTGCAGCATCATC 3' SEQ ID NO:57 CAH interrogator oligo 8 (wild type) for mutation site 3

11087 5' CCTGGAAGGGCACTT 3' SEQ ID NO:58 CAH interrogator oligo 4 (pseudogene/mutant) for mutation site 4

11146 5' CCTGGAAGGGCACGT 3' SEQ ID NO:59 CAH interrogator oligo 9 (wild type) for mutation site 4

11088 5' GATTCAGCAGCGACTGTA 3' SEQ ID NO:60 CAH interrogator oligo 5 (pseudogene/mutant) for mutation site 5

11147 5' GATTCAGCAGCGACTGCA 3' SEQ ID NO:61 CAH interrogator oligo 10 (wild type) for mutation site 5

11287 5' CGAGGTGCTGCGCCTGCG 3' SEQ ID NO:62 CAH interrogation oligo 11 (wild type) for mutation site 6

11288 5' CGAGGTGCTGCGCCTGTG 3' SEQ ID NO:63 CAH interrogation oligo 12 (pseudogene/mutant) for mutation site 6

11641 5'GGGATCACATCGTGGAGATG 3' SEQ ID NO:64 CAH interrogation oligo 23 (wild type) for mutation site 7

11642 5'GGGATCACAACGAGGAGAAG 3' SEQ ID NO:65 CAH interrogation oligo 24 (pseudogene/mutant) for mutation site 7

EXAMPLE 10
Reduction of Target Background by Removal of One Strand of a Double Strand DNA Target A particular target produced by amplification of a segment of the rice genome is interrogated in this Example. It was found that this target produces high background signal values if nothing is done to eliminate one strand of the amplified DNA target and did not exhibit discrimination between two primers that were designed to detect a SNP present in some rice strains. This Example illustrates how one can purposefully destroy one of the amplified DNA strands and interrogate the other strand. For this case in particular, such manipulations result in greatly reduced background light signals from the target, permitting clear determination of the interrogation signals.

Primers RS1 (SEQ ID NO:66) and RS2 (SEQ ID NO:67) were dissolved at a concentration of 50 pmole/$\mu$L in water. Primer RS1 contained phosphorothioate linkages at the first four 5'-terminal linkages that are not cleaved by the enzyme used in the reaction. DNA was isolated from rice and was at a concentration of 10 $\mu$g/mL. The following solution was assembled in duplicate:

| Component | Volume ($\mu$L) |
| --- | --- |
| 10X DNA Polymerase buffer without MgCl$_2$ (Promega M190A) | 5 |
| 25 mM MgCl$_2$ (Promega A351A) | 3 |
| 10 mM dNTP mixture (Promega C114A) | 1 |
| Primer RS1 (50 pmol/$\mu$L) | 1 |
| Primer RS2 (50 pmol/$\mu$L) | 1 |
| Rice genomic DNA (10 ng/$\mu$L) | 1 |
| Water | 38 |
| Taq DNA Polymerase (Promega M186A) | 1.25 U |

These solutions were heated to 94° C. for two minutes, then subjected to the following temperature cycling program for 35 cycles: 0.5 minutes, 94° C.; 1 minute, 60° C.; 1 minute, 70° C. Then the solution was held at 70° C. for 7 minutes then cooled to 4° C.

The two reaction tubes were pooled and mixed and then 3–25 $\mu$L samples were removed and placed into individual tubes. The compositions within the individual tubes were treated with T7 Exonuclease 6 (USB, E700254) as follows.

| Solution 1 | No Exo 6 addition or further heating |
| --- | --- |
| Solution 2 | 50 U of Exo 6 and heated for 15 minutes at 37° C. |
| Solution 3 | 50 U of Exo 6 and heated for 30 minutes at 37° C. |

The DNA in the resulting solutions was purified using the following method:

1. 200 $\mu$L of a slurry containing 15 $\mu$L MagneSil™ paramagnetic particles (Promega) in solution containing 0.4 M guanidine thiocyanate and 0.08 M potassium acetate were added to each sample.
2. The MagneSil™ paramagnetic particles were mixed in the solutions and held against the side of the tube with a magnet.
3. The particles were washed twice with 200 $\mu$L of 70% ethanol by addition of the solution to the tubes, resuspension of the particles in the solution, recapture of the particles against the tube walls with the magnet and removal of the particle-free solution.
4. The particles were resuspended in fifty microliters of water.
5. 200 $\mu$L 0.4 M GTC and 0.08 M potassium acetate were added to each.
6. Step 2 was repeated as described above except that three washes with 70% ethanol were performed.
7. The particles were resuspended in 100 $\mu$L water, the particles were captured against the side of the tube, and the solution containing the purified DNA was transferred to a new tube.

The following master mix was assembled:

| | |
| --- | --- |
| 10X DNA Polymerase Buffer (Promega M195) | 20 $\mu$L |
| 40 mM Sodium Pyrophosphate (Promega C113) | 5 $\mu$L |
| 10 U/$\mu$l Klenow Exo Minus (Promega M218) | 5 $\mu$L |
| NDPK (Sigma, NO379 at 10 U/$\mu$L in water) | 1 $\mu$L |
| ADP Sigma A5285, 10 $\mu$M in water) | 2 $\mu$L |
| Water | 67 $\mu$L |
| | 100 $\mu$L |

Probes RS3 (SEQ ID NO:68) and RS4 (SEQ ID NO:69) were resuspended at a concentration of 1 mg/mL in water. Each of the purified DNAs was assembled into reaction solutions as described below.

| Solution | Probe ($\mu$L) | Purified DNA Target ($\mu$L) | Water ($\mu$L) |
| --- | --- | --- | --- |
| Wild Type (WT) Probe | 1, RS3 | 4 | 15 |
| Variant Probe | 1, RS4 | 4 | 15 |
| No Probe | none | 4 | 16 |

These solutions were heated at 95° C. for 3 minutes, then placed in a 37° C. incubator for 10 minutes. After the 10 minute incubation, 20 $\mu$L of master mix were added to all tubes and the tubes were incubated again for 15 minutes at 37° C. After this second incubation, the solutions were added to 100 $\mu$l L/L reagent (Promega, F202A) and the light produced measured immediately using a Turner® TD 20/20 luminometer.

The following results were obtained:

| | Relative Light Units Measured | | |
| --- | --- | --- | --- |
| Target | WT Probe | Variant Probe | No Probe |
| No Exo 6 Treatment | 759.0 | 776.0 | 401.6 |
| 15 min. Exo 6 Treatment | 556.6 | 138.4 | 122.3 |
| 30 min. Exo 6 Treatment | 543.2 | 257.4 | 203.0 |

-continued

Calculation of Net Light Units and Ratio of Response

| Target | Net Light Units* | | |
|---|---|---|---|
| | WT Probe | Variant Probe | Ratio** |
| No Exo 6 Treatment | 357.4 | 374.4 | 0.95 |
| 15 min. Exo 6 Treatment | 434.3 | 16.1 | 27.0 |
| 30 min. Exo 6 Treatment | 340.2 | 54.4 | 6.25 |

*Net light units are calculated by subtracting the no probe value from the other two values
**Ratio is calculated by dividing the net light units for the WT probe by the net light units for the variant reaction.

The exonuclease used in this example hydrolyzes double-stranded DNA in a 5' to 3' direction, but cannot hydrolyze the DNA if phosphorothioate linkages are present on the 5' end of the DNA to be digested. Thus, the treatment used above should eliminate one strand of the amplified DNA made by extension of primer RS2 but should not eliminate the strand made by extension of primer RS1. This treatment both reduced the response of reactions without primer and permitted the discrimination of the SNP at the interrogation site.

RS1 5' C*C*C*A*ACACCTTACAGAAATTAGC 3' SEQ ID NO:66 (* signifies the presence of a phosphorothioate linkage between the indicated bases.)
RS2 5'TCTCAAGACACAAATAACTGCAG 3' SEQ ID NO:67
RS3 5'AGAACATCTGCAAGG 3' SEQ ID NO:68
RS4 5'AGAACATCTGCAAGT 3' SEQ ID NO:69

EXAMPLE 11

Determination of SNPs in DNA Isolated from Plant Materials

The procedures detailed in Example 10 are used here to determine the genotype of rice DNAs at a known SNP site.

Five coded DNA samples and two DNA samples of known genotype (the "G" allele and the "T" allele) were obtained and subjected to amplification with primers RS1 (SEQ ID NO:66) and RS2 (SEQ ID NO:67) as described in the previous Example. The DNA was then treated with T7 Exonuclease 6 for 15 minutes at 37° C. and purified as in the previous Example. The resulting purified DNA was subjected to pyrophosphorylation reactions using probes RS3 (SEQ ID NO:68), RS4 (SEQ ID NO:69), or no probe and the reaction products added to L/L reagent (Promega, F202A) and light production measured as in the previous example.

The following results were obtained:

| | Relative Light Units Measured | | |
|---|---|---|---|
| DNA Analyzed | WT Probe (RS3 G Allele) | Variant Probe (RS4 T Allele) | No Probe |
| #1 | 784.5 | 307.5 | 229.9 |
| #2 | 286.3 | 882.7 | 227.9 |
| #3 | 291.5 | 862.4 | 202.9 |
| #4 | 560.4 | 195.5 | 158.2 |
| #5 | 706.8 | 235.5 | 187.7 |
| G Allele | 810.7 | 250.0 | 189.2 |
| T Allele | 416.6 | 1121 | 243.4 |

Net Light Units, Ratio and Called Genotype

| DNA Analyzed | Net Light Units* | | | Called Genotype |
|---|---|---|---|---|
| | WT Probe | Variant Probe | Ratio** | |
| #1 | 554.6 | 77.6 | 7.1 | G Allele |
| #2 | 58.4 | 654.8 | 0.09 | T Allele |
| #3 | 88.6 | 659.5 | 0.13 | T Allele |
| #4 | 402.2 | 37.3 | 10.8 | G Allele |
| #5 | 519.1 | 47.8 | 10.9 | G Allele |
| G Allele Std. Deviation | 621.5 | 60.8 | 10.2 | G Allele |
| T Allele Std. Deviation | 173.2 | 877.6 | 0.20 | T Allele |

*Net light units = total light units - no primer values.
**Ratio = Net light units WT primer/net light units variant primer After these results were obtained, the identity of the DNA samples was uncoded and all the called genotypes agreed with the previously determined genotype of these samples. These results demonstrate the assay described in this Example can be used to determine SNPs in plant DNA and that removal of one DNA strand of a sample can help eliminate high background signals from a template, permitting SNPs to be determined.

RS1 5' C*C*C*A*ACACCTTACAGAAATTAGC 3' SEQ ID NO:66 (* signifies the presence of a phosphorothioate linkage between the indicated bases.)
RS2 5'TCTCAAGACACAAATAACTGCAG 3' SEQ ID NO:67
RS3 5'AGAACATCTGCAAGG 3' SEQ ID NO:68
RS4 5'AGAACATCTGCAAGT 3' SEQ ID NO:69

From the foregoing, it will be observed that numerous modifications and variations can be effected without departing from the true spirit and scope of the present invention. It is to be understood that no limitation with respect to the specific examples presented is intended or should be inferred. The disclosure is intended to cover by the appended claims modifications as fall within the scope of the claims.

What is claimed is:

1. A nucleic acid assay method wherein the presence or absence of a predetermined nucleic acid target sequence is determined, and a nucleic acid target-containing sequence in a nucleic acid sample to be assayed is amplified to form an amplified nucleic acid sample prior to said determination, the improvement wherein the presence or absence of said predetermined nucleic acid target sequence is determined by steps that comprise:

(A) admixing the amplified nucleic acid sample to be assayed with one or more nucleic acid probes to form a hybridization composition, wherein the 3'-terminal region of said nucleic acid probes (i) hybridizes with partial or total complementarity to at least one said predetermined nucleic acid target sequence when that sequence is present in the sample and (ii) includes an identifier nucleotide;

(B) maintaining said hybridization composition for a time period sufficient to form a treated sample that may contain said amplified predetermined nucleic acid target sequence hybridized with a nucleic acid probe;

(C) admixing the treated sample with a depolymerizing amount of an enzyme whose activity is to release one or more single nucleotides from the 3'-terminus of a hybridized nucleic acid probe to form a treated reaction mixture;

(D) maintaining the treated reaction mixture for a time period sufficient to permit the enzyme to depolymerize hybridized nucleic acid and release identifier nucleotides therefrom; and (E) analyzing for the presence of released identifier nucleotides to obtain an analytical output, the analytical output indicating the presence or absence of at least one said nucleic acid target sequence in said nucleic acid sample.

2. The method according to claim 1 wherein said identifier nucleotide is a nucleoside triphosphate.

3. The method according to claim 2 wherein said nucleoside triphosphate is used to covert ADP to ATP using a nucleoside diphosphate kinase.

4. The method according to claim 3 wherein said nucleoside diphosphate kinase is encoded by a nucleic acid sequence that comprises the nucleic acid sequence of a nucleoside diphosphate kinase encoded by *Pyrococcus furiosis*.

5. The method according to claim 1 wherein said analytical output is obtained by luminescence spectroscopy.

6. The method according to claim 1 wherein said analytical output is obtained by fluorescence spectroscopy.

7. The method according to claim 1 wherein said analytical output is obtained by mass spectrometry.

8. The method according to claim 1 wherein said analytical output is obtained by absorbance spectroscopy.

9. The method according to claim 1 wherein said nucleic acid target-containing sequence in a nucleic acid sample is amplified by rolling circle amplification.

10. The method according to claim 1 wherein said nucleic acid target-containing sequence in a nucleic acid sample is amplified by PCR amplification.

11. The method according to claim 1 wherein said nucleic acid target-containing sequence in a nucleic acid sample is amplified by ligase chain reaction amplification.

12. An amplification and interrogation process to determine the presence or absence of a predetermined nucleic acid target sequence comprising the steps of:

(A) providing a ligation reaction solution comprising (i) a ligating amount of a ligase, (ii) a nucleic acid sample that may contain a predetermined nucleic acid target sequence wherein the nucleic acid target sequence has a 3'-portion and a 5'-portion, (iii) an open circle probe comprising three regions: an open circle probe 3'-terminal region, a linker region, and an open circle probe 5'-terminal region, said open circle probe further including a detection primer target and an amplification primer target, the amplification primer target being downstream of the detection primer target, wherein upon hybridization between the open circle probe and the nucleic acid target sequence, the open circle probe 3'-terminal region is complementary to a sequence of the 3'-portion of said predetermined nucleic acid target sequence, and the open circle probe 5'-terminal region is complementary to a sequence of the 5'-portion of said predetermined nucleic acid target sequence, and (iv) optionally further comprising a polymerizing amount of a DNA polymerase and deoxynucleoside triphosphates when the hybridized open circle probe 3'-terminus is not adjacent and ligatable to the hybridized open circle probe 5'-terminus and a gap is present between those termini;

(B) maintaining the ligation reaction solution for a time period sufficient to permit filling-in of said gap, when present, and ligation of the termini of the open circle probe to form a closed circular probe and a treated ligation reaction solution;

(C) admixing said closed circular probe with an amplification primer that hybridizes with said amplification primer target, nucleoside triphosphates, and a polymerizing amount of a DNA polymerase to form a replication reaction mixture;

(D) maintaining the replication reaction mixture for a time period sufficient to permit extension of a nucleic acid strand from the amplification primer, wherein the extension product nucleic acid strand comprises an interrogation target that is complementary to the detection primer target, to form a treated replication mixture;

(E) admixing an interrogation probe with the treated replication mixture, wherein the interrogation probe is complementary to said interrogation target and comprises an identifier nucleotide in the 3'-terminal region;

(F) denaturing the treated replication mixture to form a denatured mixture;

(G) annealing the denatured mixture to form hybrid between the interrogation probe and the interrogation target when present to form an interrogation solution;

(H) admixing a depolymerizing amount of an enzyme whose activity is to release one or more single nucleotides from the 3'-terminus of a hybridized nucleic acid probe with the interrogation solution to form a depolymerization reaction mixture;

(I) maintaining the depolymerization reaction mixture for a time period sufficient to permit the enzyme to depolymerize hybridized nucleic acid and release identifier nucleotide therefrom; and (J) analyzing for the presence of released identifier nucleotide to obtain an analytical output, the analytical output indicating the presence or absence of said predetermined nucleic acid target sequence.

13. The process according to claim 12 wherein the depolymerizing enzyme is thermostable.

14. The process according to claim 12 wherein free nucleotide triphosphates are separated from the treated replication mixture prior to step H.

15. The process according to claim 12 wherein step H occurs before step F.

16. The process according to claim 12 wherein there is a gap present between the termini of the hybridized open circle probe, the portion of the predetermined nucleic acid target sequence between the 3'- and 5'-termini of the hybridized open circle probe that is opposite said gap contains three or fewer nucleotides and only nucleoside triphosphates complementary to said three or fewer nucleotides are present in said ligation reaction solution.

17. The process according to claim 12 wherein a polymerizing amount of a DNA polymerase and nucleoside triphosphates are present in said ligation reaction solution.

18. The process according to claim 12 wherein the open circle probe comprises a plurality of detection primer targets.

19. The process according to claim 12 wherein the presence or absence of a plurality of predetermined nucleic acid targets is determined using a plurality of detection probes comprising different identifier nucleotides.

20. The method according to claim 12 wherein said identifier nucleotide is a nucleoside triphosphate.

21. The method according to claim 20 wherein said nucleoside triphosphate is used to covert ADP to ATP using a nucleoside diphosphate kinase.

22. The method according to claim 21 wherein said nucleoside diphosphate kinase is encoded by a nucleic acid sequence that comprises the nucleic acid sequence of a nucleoside diphosphate kinase encoded by Pyrococcus furiosis.

23. The method according to claim 12 wherein said analytical output is obtained by luminescence spectroscopy.

24. The method according to claim 12 wherein said analytical output is obtained by fluorescence spectroscopy.

25. The method according to claim 12 wherein said analytical output is obtained by mass spectrometry.

26. The method according to claim 12 wherein said analytical output is obtained by absorbance spectroscopy.

27. The method according to claim 12 wherein said nucleic acid sample is obtained from a biological sample.

28. The method according to claim 27 wherein said predetermined nucleic acid target sequence is a microbial or viral nucleic acid.

29. The method according to claim 28 wherein said predetermined nucleic acid target sequence is a viral nucleic acid and the magnitude of the analytical output from a predetermined amount of said biological fluid provides a measure of the viral load in the biological sample.

30. The method according to claim 12 wherein said nucleic acid sample is obtained from a food source.

31. The method according to claim 30 wherein said food source is a plant.

32. The method according to claim 31 wherein said predetermined nucleic acid target sequence is a sequence non-native to the genome of said plant.

33. An amplification and interrogation process to determine the presence or absence of a predetermined nucleic acid target sequence having a 3'-portion and a 5'-portion comprising the steps of:

(A) providing a ligation reaction solution comprising (i) ligating amount of a ligase, (ii) a nucleic acid sample that may contain a predetermined nucleic acid target sequence wherein the nucleic acid target sequence has a 3'-portion and a 5'-portion, (iii) a pair of ligation probes, the first ligation probe being complementary to the 5'-portion of the nucleic acid target sequence and the second ligation probe being complementary to the 3'-portion of the nucleic acid target sequence, wherein said first ligation probe includes an amplification primer target and a 3'-terminus and said second ligation probe includes a detection primer target and a 5'-terminus, wherein upon hybridization between the pair of ligation probes and the nucleic acid target sequence, the second ligation probe is complementary to a sequence of the 3'-portion of said predetermined nucleic acid target sequence, and the first ligation probe is complementary to a sequence of the 5'-portion of said predetermined nucleic acid target sequence, and (iv) optionally further comprising a polymerizing amount of a DNA polymerase and deoxynucleoside triphosphates when the hybridized second ligation probe 3'-terminus is not adjacent and ligatable to the hybridized first ligation probe 5'-terminus and a gap is present between those termini;

(B) maintaining the ligation reaction solution for a time period sufficient to permit filling-in of said gap, when present, and ligation of the termini of the pair of ligation probes to form a ligated probe and a treated ligation reaction solution;

(C) admixing said ligated probe with an amplification primer that hybridizes with said amplification primer target, nucleoside triphosphates, and a polymerizing amount of a DNA polymerase to form a replication reaction mixture;

(D) maintaining the replication reaction mixture for a time period sufficient to permit extension of a nucleic acid strand from the amplification primer, wherein the extension product nucleic acid strand comprises a interrogation target that is complementary to the detection primer target, to form a treated amplification mixture;

(E) admixing an interrogation probe with the treated amplification mixture, wherein the interrogation probe is complementary to said interrogation target and comprises an identifier nucleotide in the 3'-terminal region;

(F) denaturing the treated amplification mixture to form a denatured mixture;

(G) annealing the denatured mixture to form hybrid between the interrogation probe and the interrogation target when present to form an interrogation solution;

(H) admixing a depolymerizing amount of an enzyme whose activity is to release one or more single nucleotides from the 3'-terminus of a hybridized nucleic acid probe with the interrogation solution to form a depolymerization reaction mixture;

(I) maintaining the depolymerization reaction mixture for a time period sufficient to permit the enzyme to depolymerize hybridized nucleic acid and release identifier nucleotide therefrom; and (J) analyzing for the release of identifier nucleotide to obtain an analytical output, the analytical output indicating the presence or absence of said predetermined nucleic acid target sequence.

34. The process according to claim 33 wherein the depolymerizing enzyme is thermostable.

35. The process according to claim 33 wherein free nucleotide triphosphates are separated from the treated amplification mixture prior to step H.

36. The process according to claim 33 wherein step H occurs before step F.

37. The process according to claim 33 wherein there is a gap present between the termini of the hybridized pair of ligation probes, the portion of the predetermined nucleic acid target sequence between the 3'- and 5'-termini of the hybridized pair of ligation probes that is opposite said gap contains three or fewer nucleotides and only nucleoside triphosphates complementary to said three or fewer nucleotides are present in said ligation reaction solution.

38. The process according to claim 33 wherein a polymerizing amount of a DNA polymerase and nucleoside triphosphates are present in said ligation reaction solution.

39. The process according to claim 33 wherein said second ligation probe comprises a plurality of detection primer targets.

40. The process according to claim 33 wherein the presence or absence of a plurality of predetermined nucleic acid targets is determined using a plurality of detection probes comprising different identifier nucleotides.

41. The method according to claim 33 wherein said analytical output is obtained by luminescence spectroscopy.

42. The method according to claim 33 wherein said analytical output is obtained by fluorescence spectroscopy.

43. The method according to claim 33 wherein said analytical output is obtained by mass spectrometry.

44. The method according to claim 33 wherein said analytical output is obtained by absorbance spectroscopy.

45. The method according to claim 33 wherein said nucleic acid sample is obtained from a biological sample.

46. The method according to claim 45 wherein said predetermined nucleic acid target sequence is a microbial or viral nucleic acid.

47. The method according to claim 46 wherein said predetermined nucleic acid target sequence is a viral nucleic acid and the magnitude of the analytical output from a predetermined amount of said biological fluid provides a measure of the viral load in the biological sample.

48. The method according to claim 33 wherein said nucleic acid sample is obtained from a food source.

49. The method according to claim 48 wherein said food source is a plant.

50. The method according to claim 49 herein said predetermined nucleic acid target sequence is a sequence non-native to the genome of said plant.

51. A method for determining the presence or absence of a restriction endonuclease recognition sequence in a nucleic acid sample that comprises the steps of:

(A) providing a treated sample that may contain a hybridized nucleic acid target that is a cleaved restriction endonuclease recognition sequence that includes an identifier nucleotide in the restriction endonuclease recognition sequence;

(B) admixing the treated sample with a depolymerizing amount of an enzyme whose activity is to release one or more single nucleotides from the 3'-terminus of a restriction endonuclease recognition sequence to form a treated reaction mixture;

(C) maintaining the treated reaction mixture for a time period sufficient to permit the enzyme to depolymerize hybridized nucleic acid and release identifier nucleotide therefrom; and (D) analyzing for the presence of released identifier nucleotide to obtain an analytical output, the analytical output indicating the presence or absence of said restriction endonuclease recognition sequence.

52. The method of claim 51 including the further steps of forming a treated sample by:

(A) providing an endonuclease cleavage reaction solution comprising a nucleic acid sample and a restriction endonuclease enzyme specific for the restriction endonuclease recognition sequence; and (B) maintaining the endonuclease cleavage reaction solution for a time period sufficient for the restriction endonuclease enzyme to cleave the restriction endonuclease recognition sequence to form a treated sample.

53. The method of claim 51 including the further step of amplifying a nucleic acid target sequence in a nucleic acid sample prior to providing said restriction endonuclease recognition sequence.

54. The method of claim 53 wherein said nucleic acid target sequence is amplified by the further steps of:

(A) admixing a crude nucleic acid sample with PCR amplification primers that are complementary to regions upstream and downstream of the nucleic acid target sequence and a template-dependent polymerase to form an amplification sample mixture wherein either the nucleic acid target sequence or the PCR amplification primers includes a restriction endonuclease recognition sequence;

(B) maintaining the amplification sample mixture for a time period sufficient to denature the nucleic acid target sequence to form a denatured amplification reaction mixture;

(C) annealing the denatured amplification reaction mixture for a time period sufficient for PCR amplification primers to anneal to the nucleic acid target sequence to form an amplification reaction mixture; and (D) maintaining the amplification reaction mixture for a time period sufficient to permit the template-dependent polymerase to extend the nucleic acid from the PCR primers to form an amplified nucleic acid sample.

55. The method according to claim 51 wherein said identifier nucleotide is a nucleoside triphosphate.

56. The method according to claim 55 wherein said nucleoside triphosphate is used to covert ADP to ATP using a nucleoside diphosphate kinase.

57. The method according to claim 56 wherein said nucleoside diphosphate kinase is encoded by a nucleic acid sequence that comprises the nucleic acid sequence of a nucleoside diphosphate kinase encoded by *Pyrococcus furiosis*.

58. The method according to claim 51 wherein said analytical output is obtained by luminescence spectroscopy.

59. The method according to claim 51 wherein said analytical output is obtained by absorbance spectrometry.

60. The method according to claim 51 wherein said analytical output is obtained by fluorescence spectroscopy.

61. The method according to claim 51 wherein said analytical output is obtained by mass spectrometry.

62. The method according to claim 51 wherein said enzyme whose activity is to release nucleotides is a template-dependent polymerase that, in the presence of pyrophosphate ions, depolymerizes hybridized nucleic acids whose bases in the 3'-terminal region are completely complementary to bases of said nucleic acid target.

* * * * *